(12) United States Patent
Goren et al.

(10) Patent No.: US 8,580,503 B2
(45) Date of Patent: Nov. 12, 2013

(54) METHODS AND COMPOSITIONS FOR DIAGNOSING COMPLICATIONS OF PREGNANCY

(75) Inventors: Yaron Goren, Kefar Hass (IL); Shlomit Gilad, Gani Hadar (IL); Moshe Hod, Herzelia (IL); Yariv Yogev, Ramat Aviv (IL)

(73) Assignees: Rosetta Genomics Ltd., Rehovot (IL); Mor Research Applications, Tel Aviv (IL)

( * ) Notice: Subject to any disclaimer, the term of this patent is extended or adjusted under 35 U.S.C. 154(b) by 476 days.

(21) Appl. No.: 12/864,424

(22) PCT Filed: Jan. 26, 2009

(86) PCT No.: PCT/IL2009/000101
§ 371 (c)(1), (2), (4) Date: Jul. 23, 2010

(87) PCT Pub. No.: WO2009/093254
PCT Pub. Date: Jul. 30, 2009

(65) Prior Publication Data
US 2010/0291585 A1    Nov. 18, 2010

Related U.S. Application Data

(60) Provisional application No. 61/040,671, filed on Mar. 30, 2008, provisional application No. 61/023,859, filed on Jan. 27, 2008.

(51) Int. Cl.
*C12Q 1/68* (2006.01)
(52) U.S. Cl.
USPC .......................... 435/6.11; 435/6.1; 435/6.12
(58) Field of Classification Search
None
See application file for complete search history.

(56) References Cited

U.S. PATENT DOCUMENTS

| | | | |
|---|---|---|---|
| 5,034,506 | A | 7/1991 | Summerton et al. |
| 5,235,033 | A | 8/1993 | Summerton et al. |
| 6,506,559 | B1 | 1/2003 | Fire et al. |
| 7,232,806 | B2 | 6/2007 | Tuschl et al. |
| 7,642,348 | B2 | 1/2010 | Bentwich et al. |
| 7,718,367 | B2 | 5/2010 | Lo et al. |
| 7,745,608 | B2 | 6/2010 | Manoharan et al. |
| 7,825,229 | B2 | 11/2010 | Itzhak et al. |
| 2005/0059005 | A1 | 3/2005 | Tuschl et al. |
| 2005/0182005 | A1 | 8/2005 | Tuschl et al. |
| 2006/0252068 | A1 | 11/2006 | Lo et al. |

FOREIGN PATENT DOCUMENTS

| | | |
|---|---|---|
| EP | 1777301 | 4/2007 |
| WO | WO 03/078450 A2 | 9/2003 |
| WO | WO 2006/137941 A2 | 12/2006 |
| WO | WO 2009/015357 A1 | 1/2009 |
| WO | WO 2009/093254 A3 | 7/2009 |

OTHER PUBLICATIONS

U.S. Appl. No. 11/384,049, filed Mar. 17, 2006.
Bartel, et al., "MicroRNAs: At the Root of Plant Development?," *Plant Physiology*, Jun. 2003, pp. 709-717, vol. 132.
Bartel, et al., "MicroRNAs: Genomics, Biogenesis, Mechanism and Function", Cell, 2004, vol. 116, pp. 281-297.
Brennecke, et al., "Principles of MicroRNA-Target Recognition", *PLoS Biology*, 2005, vol. 3, No. 3, p. e85.
Chim, et al., "Detection and Characterization of Placental MicroRNAs in Maternal Plasma", *Clinical Chemistry*, vol. 54, No. 3, 2008, pp. 482-490.
Doench, et al., "Specificity of microRNA target selection in translational respression", Genes & Development, 2004, pp. 1-7.
EP Supplemental Search Report for EP Application No. EP09703376.5, dated Mar. 25, 2011.
Griffiths-Jones, et al., "miRBase: microRNA sequences, targets and gene nomenclature", *Nucleic Acids Research*, 2006, vol. 34, pp. D140-D144.
Hofacker, et al., "Fast folding and comparison of RNA secondary structures", *Monatshefte fur Chemie (Chemical Monthly)*, 1994, vol. 125, pp. 167-188.
Krek, et al., "Combinatorial microRNA target predictions", *Nature Genetics*, 2005, pp. 1-5.
Krutzfeldt, et al., "Silencing of microRNAs in vivo with 'antagomirs,'" *Nature*, 2005, pp. 1-5.
Lewis, et al., "Conserved seed pairing, oftern flanked by adenosines, indicates that thousands of human genes are microRNA targets", *Cell*, 2005, vol. 120, pp. 15-20.
Pineles, et al., "Distinct subsets of microRNAs are expressed differentially in the human placentas of patients with preeclampsia", *American Journal of Obstetrics& Gynecology*, Mar. 2007, vol. 196, No. 3, p. 261.e1.
Shi, et al., "Facile means for quantifying microRNA expression by real-time PCR", *BioTechniques*, 2005, vol. 39, pp. 519-525.
Soutschek, et al., "Therapeutic silencing of an endogenous gene by systemic administration of modified siRNAs," *Nature*, Nov. 2004, pp. 173-178, vol. 432.
Yekta, et al., "MicroRNA-Directed Cleavage of *HOXB8* mRNA," *Science*, Apr. 2004, pp. 594-596, vol. 304.
Yogev, et al., "110: Spontaneous preterm labor—a possible role for micro-RNA", *American Journal of Obstetrics & Gynecology*, 2007, vol. 197, No. 6, p. S44.
Yogev, et al., "459: Micro RNA: A Central new player in post-transcriptional regulation pathway in preeclampsia", *American Journal of Obstetrics & Gynecology*, 2007, vol. 197, No. 6, p. S135.
The International Search Report from the corresponding International Patent Application No. PCT/IL09/00101, dated Jul. 9, 2009.

*Primary Examiner* — James Martinell
(74) *Attorney, Agent, or Firm* — Foley & Lardner LLP

(57) ABSTRACT

The present invention provides methods and compositions for identifying subjects at risk of developing a complication of pregnancy, such as preeclampsia or preterm labor. The compositions are microRNAs and associated nucleic acids.

8 Claims, 13 Drawing Sheets

SEQUENCE LISTING

<160> NUMBER OF SEQ ID NOS: 110

<210> SEQ ID NO 1
<211> LENGTH: 24
<212> TYPE: RNA

<213> ORGANISM: Homo sapiens

<400> SEQUENCE: 1
uucuccaaaa gaaagcacuu ucug                     24

<210> SEQ ID NO 2
<211> LENGTH: 23
<212> TYPE: RNA
<213> ORGANISM: Homo sapiens

<400> SEQUENCE: 2
gaacgcgcuu cccuauagag ggu                      23

<210> SEQ ID NO 3
<211> LENGTH: 22
<212> TYPE: RNA
<213> ORGANISM: Homo sapiens

<400> SEQUENCE: 3
cuacaaaggg aagcacuuuc uc                       22

<210> SEQ ID NO 4
<211> LENGTH: 23
<212> TYPE: RNA
<213> ORGANISM: Homo sapiens

<400> SEQUENCE: 4
aaaccguuac cauuacugag uuu                      23

<210> SEQ ID NO 5
<211> LENGTH: 21
<212> TYPE: RNA
<213> ORGANISM: Homo sapiens

<400> SEQUENCE: 5
ggcaagaugc uggcauagcu g                        21

<210> SEQ ID NO 6
<211> LENGTH: 22
<212> TYPE: RNA
<213> ORGANISM: Homo sapiens

<400> SEQUENCE: 6
uuagggugcu uagcuguuaa cu                       22

<210> SEQ ID NO 7
<211> LENGTH: 22
<212> TYPE: RNA
<213> ORGANISM: Homo sapiens

<400> SEQUENCE: 7
cugugcgugu gacagcggcu ga                       22

<210> SEQ ID NO 8
<211> LENGTH: 22
<212> TYPE: RNA
<213> ORGANISM: Homo sapiens

<400> SEQUENCE: 8
cgggguuuug agggcgagau ga                       22

<210> SEQ ID NO 9
<211> LENGTH: 23
<212> TYPE: RNA

<213> ORGANISM: Homo sapiens

<400> SEQUENCE: 9
aauggcgcca cuaggguugu gca                                          23

<210> SEQ ID NO 10
<211> LENGTH: 22
<212> TYPE: RNA
<213> ORGANISM: Homo sapiens

<400> SEQUENCE: 10
uacccuguag aaccgaauuu gu                                           22

<210> SEQ ID NO 11
<211> LENGTH: 23
<212> TYPE: RNA
<213> ORGANISM: Homo sapiens

<400> SEQUENCE: 11
uauggcacug guagaauuca cug                                          23

<210> SEQ ID NO 12
<211> LENGTH: 23
<212> TYPE: RNA
<213> ORGANISM: Homo sapiens

<400> SEQUENCE: 12
uccaguacca cgugucaggg cca                                          23

<210> SEQ ID NO 13
<211> LENGTH: 21
<212> TYPE: RNA
<213> ORGANISM: Homo sapiens

<400> SEQUENCE: 13
uagcaccauc ugaaaucggu u                                            21

<210> SEQ ID NO 14
<211> LENGTH: 22
<212> TYPE: RNA
<213> ORGANISM: Homo sapiens

<400> SEQUENCE: 14
uuuaacaugg ggguaccugc ug                                           22

<210> SEQ ID NO 15
<211> LENGTH: 21
<212> TYPE: RNA
<213> ORGANISM: Homo sapiens

<400> SEQUENCE: 15
uaguagaccg uauagcguac g                                            21

<210> SEQ ID NO 16
<211> LENGTH: 22
<212> TYPE: RNA
<213> ORGANISM: Homo sapiens

<400> SEQUENCE: 16
aaagugcuuc ccuuuggacu gu                                           22

<210> SEQ ID NO 17
<211> LENGTH: 23
<212> TYPE: RNA

```
<213> ORGANISM: Homo sapiens

<400> SEQUENCE: 17
uggaguguga caauguguuu ugu                                        23

<210> SEQ ID NO 18
<211> LENGTH: 22
<212> TYPE: RNA
<213> ORGANISM: Homo sapiens

<400> SEQUENCE: 18
cugugcgugu gacagcggcu ga                                         22

<210> SEQ ID NO 19
<211> LENGTH: 21
<212> TYPE: RNA
<213> ORGANISM: Homo sapiens

<400> SEQUENCE: 19
ugucaguuug ucaaauaccc c                                          21

<210> SEQ ID NO 20
<211> LENGTH: 22
<212> TYPE: RNA
<213> ORGANISM: Homo sapiens

<400> SEQUENCE: 20
uacaguaguc ugcacauugg uu                                         22

<210> SEQ ID NO 21
<211> LENGTH: 22
<212> TYPE: RNA
<213> ORGANISM: Homo sapiens

<400> SEQUENCE: 21
aacgcacuuc ccuuuagagu gu                                         22

<210> SEQ ID NO 22
<211> LENGTH: 23
<212> TYPE: RNA
<213> ORGANISM: Homo sapiens

<400> SEQUENCE: 22
aaagugcauc cuuuuagagg uuu                                        23

<210> SEQ ID NO 23
<211> LENGTH: 22
<212> TYPE: RNA
<213> ORGANISM: Homo sapiens

<400> SEQUENCE: 23
acauagagga aauuccacgu uu                                         22

<210> SEQ ID NO 24
<211> LENGTH: 22
<212> TYPE: RNA
<213> ORGANISM: Homo sapiens

<400> SEQUENCE: 24
cuggacuuag ggucagaagg cc                                         22

<210> SEQ ID NO 25
<211> LENGTH: 22
<212> TYPE: RNA
```

<213> ORGANISM: Homo sapiens

<400> SEQUENCE: 25
cuggacuugg agucagaagg cc                                          22

<210> SEQ ID NO 26
<211> LENGTH: 87
<212> TYPE: RNA
<213> ORGANISM: Homo sapiens

<400> SEQUENCE: 26
ucucaggcug ugacccucca aagggaagaa cuuucuguug ucuaaaagaa aagaacgcac  60
uucccuuuag aguguuaccg ugugaga                                     87

<210> SEQ ID NO 27
<211> LENGTH: 87
<212> TYPE: RNA
<213> ORGANISM: Homo sapiens

<400> SEQUENCE: 27
ucucaugcug ugacccucua gagggaagcg cuuucuguug ucugaaagaa aagaacgcgc  60
uucccuauag aggguuaccc uuugaga                                     87

<210> SEQ ID NO 28
<211> LENGTH: 87
<212> TYPE: RNA
<213> ORGANISM: Homo sapiens

<400> SEQUENCE: 28
ucucaugcug ugacccuaca aagggaagca cuuucucuug uccaaaggaa agaaggcgc   60 uucccuuugg aguguuacgg uuugaga                                     87

<210> SEQ ID NO 29
<211> LENGTH: 85
<212> TYPE: RNA
<213> ORGANISM: Homo sapiens

<400> SEQUENCE: 29
ggcacuuggg aauggcaagg aaaccguuac cauuacugag uuuaguaaug guaauggeuuc 60 ucuugcuaua cccagaaaac gugcc                                       85

<210> SEQ ID NO 30
<211> LENGTH: 55
<212> TYPE: RNA
<213> ORGANISM: Homo sapiens

<400> SEQUENCE: 30
ggcaagaugc uggcauagcu guugaacugg gaaccugcua ugccaacaua uugcc        55

<210> SEQ ID NO 31
<211> LENGTH: 108
<212> TYPE: RNA
<213> ORGANISM: Homo sapiens

<400> SEQUENCE: 31
guagauugaa gccaguugau uagggugcuu agcuguuaac uaaguguuug uggguuuaag  60
ucccauuggu cuaguaaggg cuuagcuuaa uuaaaguggc ugauuugc              108

<210> SEQ ID NO 32
<211> LENGTH: 84
<212> TYPE: RNA

<213> ORGANISM: Homo sapiens

<400> SEQUENCE: 32
ccaggcgcag ggcagccccu gcccaccgca cacugcgcug ccccagaccc acugugcgug    60
ugacagcggc ugaucugugc cugg                                          84

<210> SEQ ID NO 33
<211> LENGTH: 83
<212> TYPE: RNA
<213> ORGANISM: Homo sapiens

<400> SEQUENCE: 33
guggucucag aaucgggguu uugagggcga gaugaguuua uguuuuaucc aacuggcccu    60
caaagucccg cuuuuggggu cau                                           83

<210> SEQ ID NO 34
<211> LENGTH: 87
<212> TYPE: RNA
<213> ORGANISM: Homo sapiens

<400> SEQUENCE: 34
ggcuaugcac ugcacaaccc uaggagaggg ugccauucac auagacuaua auugaauggc    60
gccacuaggg uugugcagug cacaacc                                       87

<210> SEQ ID NO 35
<211> LENGTH: 86
<212> TYPE: RNA
<213> ORGANISM: Homo sapiens

<400> SEQUENCE: 35
cguugucuau auauacccug uagaaccgaa uuuguguggu auccguauag ucacagauuc    60
gauucuaggg gaauauaugg ucgaug                                        86

<210> SEQ ID NO 36
<211> LENGTH: 80
<212> TYPE: RNA
<213> ORGANISM: Homo sapiens

<400> SEQUENCE: 36
cuguucugug uauggcacug guagaauuca cugugaacag ucucagucag ugaauuaccg    60
aagggccaua aacagagcag                                               80

<210> SEQ ID NO 37
<211> LENGTH: 70
<212> TYPE: RNA
<213> ORGANISM: Homo sapiens

<400> SEQUENCE: 37
gagccuccag uaccacgugu cagggccaca ugagcugggc cucgugggcc ugaugugcug    60
cuggggccuc                                                          70

<210> SEQ ID NO 38
<211> LENGTH: 99
<212> TYPE: RNA
<213> ORGANISM: Homo sapiens

<400> SEQUENCE: 38
uucugugacc ccuuagagga ugacugauuu cuuuugugu ucagucaa uauaauuuuc       60 uagccaccauc ugaaaucggu uauaaugauu ggggaagag                         99

```
<210> SEQ ID NO 39
<211> LENGTH: 66
<212> TYPE: RNA
<213> ORGANISM: Homo sapiens

<400> SEQUENCE: 39
cuuugcuuua acauggggu accugcugug ugaaacaaaa guaagugcuu ccauguuuca    60
guggag                                                             66

<210> SEQ ID NO 40
<211> LENGTH: 80
<212> TYPE: RNA
<213> ORGANISM: Homo sapiens

<400> SEQUENCE: 40
gguacuugga gagauaguag accguauagc guacgcuuua ucugugacgu auguaacacg   60
guccacuaac ccucaguauc                                               80

<210> SEQ ID NO 41
<211> LENGTH: 85
<212> TYPE: RNA
<213> ORGANISM: Homo sapiens

<400> SEQUENCE: 41
cucaggcugu gacccuccag agggaaguac uuucuguugu cugagagaaa agaaagugcu   60
ucccuuugga cuguuucggu uugag                                         85

<210> SEQ ID NO 42
<211> LENGTH: 83
<212> TYPE: RNA
<213> ORGANISM: Homo sapiens

<400> SEQUENCE: 42
cuuagcagag cuguggagug ugacaauggu guuugugucu aaacuaucaa acgccauuau   60
cacacuaaau agcuacugcu agg                                           83

<210> SEQ ID NO 43
<211> LENGTH: 84
<212> TYPE: RNA
<213> ORGANISM: Homo sapiens

<400> SEQUENCE: 43
ccaggcgcag ggcagccccu gcccaccgca cacugcgcug cccagacccc acugugcgug   60
ugacagcggc ugaucugugc cugg                                          84

<210> SEQ ID NO 44
<211> LENGTH: 132
<212> TYPE: RNA
<213> ORGANISM: Homo sapiens

<400> SEQUENCE: 44
gcucuuggcc uggccuccug cagugccacg cuccguguau uugacaagcu gaguggaca    60 cuccaugugg uagaguguca guuugucaaa uaccccaagu gcggcacaug cuuaccagcu  120
cuaggccagg gc                                                      132

<210> SEQ ID NO 45
<211> LENGTH: 83
<212> TYPE: RNA
<213> ORGANISM: Homo sapiens
```

```
<400> SEQUENCE: 45
ggccccgcca acccagugnu cagacuaccu guucaggagg cucucaaugu guacaguagu      60
cugcacauug guuaggcugg gcu                                              83

<210> SEQ ID NO 46
<211> LENGTH: 87
<212> TYPE: RNA
<213> ORGANISM: Homo sapiens

<400> SEQUENCE: 46
ucucaggcug ugacccucca aagggaagaa cuuucuguug ucuaaaagaa aagaacgcac      60
uucccuuuag aguguuaccg ugugaga                                          87

<210> SEQ ID NO 47
<211> LENGTH: 88
<212> TYPE: RNA
<213> ORGANISM: Homo sapiens

<400> SEQUENCE: 47
ucccaugcug ugacccucua gagggaagcg cuuucuguug ucugaaagaa aagaaagugc      60
auccuuuuag agguuuacug uuugagga                                         88

<210> SEQ ID NO 48
<211> LENGTH: 86
<212> TYPE: RNA
<213> ORGANISM: Homo sapiens

<400> SEQUENCE: 48
uuugguauuu aaaaggugga uauuccuucu auguuuaugu uauuuauggu uaaacauaga      60
ggaaauucca cguuuucagu aucaaa                                           86

<210> SEQ ID NO 49
<211> LENGTH: 111
<212> TYPE: RNA
<213> ORGANISM: Homo sapiens

<400> SEQUENCE: 49
gcccacaaug ugaggacacg agagaagcac uggacuuagg gucagaaggc cugagucucu      60
cugcugcaga ugggcucucu gucccugagc caagcuuugu ccucccuggg c               111

<210> SEQ ID NO 50
<211> LENGTH: 198
<212> TYPE: RNA
<213> ORGANISM: Homo sapiens

<400> SEQUENCE: 50
gaggcugcga ggagugagcg gcuuguaugg gaccaugcag ccagagggug acagagccac      60
ccagggcucc ugacuccagg uccugugugu uaccuagaaa uagcacugga cuuggaguca     120
gaaggccuga guggagucac cuuccccacu cucuggcugg ugaccccgg agcaagccau      180 uugaacucuc cgagccuc                                                   198

<210> SEQ ID NO 51
<211> LENGTH: 21
<212> TYPE: RNA
<213> ORGANISM: Homo sapiens

<400> SEQUENCE: 51
agagguagua gguugcauag u                                                21
```

```
<210> SEQ ID NO 52
<211> LENGTH: 87
<212> TYPE: RNA
<213> ORGANISM: Homo sapiens

<400> SEQUENCE: 52
ccuaggaaga gguaguaggu ugcauaguuu uagggcaggg auuuugccca caaggaggua    60
acuauacgac cugcugccuu ucuuagg                                        87

<210> SEQ ID NO 53
<211> LENGTH: 21
<212> TYPE: RNA
<213> ORGANISM: Homo sapiens

<400> SEQUENCE: 53
cugcaaaggg aagcccuuuc u                                              21

<210> SEQ ID NO 54
<211> LENGTH: 85
<212> TYPE: RNA
<213> ORGANISM: Homo sapiens

<400> SEQUENCE: 54
ucucaagcug ugacugcaaa gggaagcccu uucguuguc uaaaagaaaa gaaagugcuu    60
cccuuuggug aauuacgguu ugaga                                          85

<210> SEQ ID NO 55
<211> LENGTH: 85
<212> TYPE: RNA
<213> ORGANISM: Homo sapiens

<400> SEQUENCE: 55
ucucaagcug ugacugcaaa gggaagcccu uucguuguc ugaaagaaga gaaagcgcuu    60 cccuugcug gauuacgguu ugaga                                           85

<210> SEQ ID NO 56
<211> LENGTH: 87
<212> TYPE: RNA
<213> ORGANISM: Homo sapiens

<400> SEQUENCE: 56
ucucaagcug ugggucugca aagggaagcc cuuucguuug ucuaaaagaa gagaaagcgc    60
uucccuuugc uggauuacgg uuugaga                                        87

<210> SEQ ID NO 57
<211> LENGTH: 21
<212> TYPE: RNA
<213> ORGANISM: Homo sapiens

<400> SEQUENCE: 57
agagguagua gguugcauag u                                              21

<210> SEQ ID NO 58
<211> LENGTH: 87
<212> TYPE: RNA
<213> ORGANISM: Homo sapiens

<400> SEQUENCE: 58
ccuaggaaga gguaguaggu ugcauaguuu uagggcaggg auuuugccca caaggaggua    60
acuauacgac cugcugccuu ucuuagg                                        87
```

```
<210> SEQ ID NO 59
<211> LENGTH: 22
<212> TYPE: RNA
<213> ORGANISM: Homo sapiens

<400> SEQUENCE: 59
ugagguagua gguuguaugg uu                                                  22

<210> SEQ ID NO 60
<211> LENGTH: 84
<212> TYPE: RNA
<213> ORGANISM: Homo sapiens

<400> SEQUENCE: 60
gcauccgggu ugagguagua gguuguaugg uuuagaguua cacccuggga guuaacugua         60
caaccuucua gcuuccuug gagc                                                 84

<210> SEQ ID NO 61
<211> LENGTH: 22
<212> TYPE: RNA
<213> ORGANISM: Homo sapiens

<400> SEQUENCE: 61
uggaguguga caauguguu ug                                                   22

<210> SEQ ID NO 62
<211> LENGTH: 85
<212> TYPE: RNA
<213> ORGANISM: Homo sapiens

<400> SEQUENCE: 62
ccuuagcaga gcuguggagu gugacaaugg uguuugguc uaaacuauca aacgccauua          60
ucacacuaaa uagcuacugc uaggc                                               85

<210> SEQ ID NO 63
<211> LENGTH: 22
<212> TYPE: RNA
<213> ORGANISM: Homo sapiens

<400> SEQUENCE: 63
ugagguagua gguuguauag uu                                                  22

<210> SEQ ID NO 64
<211> LENGTH: 80
<212> TYPE: RNA
<213> ORGANISM: Homo sapiens

<400> SEQUENCE: 64
ugggaugagg uaguagguug uauaguuuua ggucacacc caccacuggg agauaacuau          60
acaaucuacu gucuuuccua                                                     80

<210> SEQ ID NO 65
<211> LENGTH: 72
<212> TYPE: RNA
<213> ORGANISM: Homo sapiens

<400> SEQUENCE: 65
agguugaggu aguagguugu auaguuuaga auuacaucaa gggagauaac uguacagccu         60
ccuagcuuuc cu                                                             72

<210> SEQ ID NO 66
```

```
<211> LENGTH: 74
<212> TYPE: RNA
<213> ORGANISM: Homo sapiens

<400> SEQUENCE: 66
gggugaggua guagguugua aguuuggggg cucugcccug cuaugggaua acuauacaau      60
cuacugucuu uccu                                                        74

<210> SEQ ID NO 67
<211> LENGTH: 85
<212> TYPE: RNA
<213> ORGANISM: Homo sapiens

<400> SEQUENCE: 67
cucaggcugu gacccucuag agggaagcac uuucuguugc uugaaagaag agaaagcgcu      60
uccuuuuaga ggauuacucu uugag                                            85

<210> SEQ ID NO 68
<211> LENGTH: 65
<212> TYPE: RNA
<213> ORGANISM: Homo sapiens

<400> SEQUENCE: 68
gugacccucu agagggaagc acuuucuguu gaaagaaaag aacaugcauc cuuucagagg      60
guuac                                                                  65

<210> SEQ ID NO 69
<211> LENGTH: 20
<212> TYPE: RNA
<213> ORGANISM: Homo sapiens

<400> SEQUENCE: 69
cuacaaaggg aagcccuuuc                                                  20

<210> SEQ ID NO 70
<211> LENGTH: 87
<212> TYPE: RNA
<213> ORGANISM: Homo sapiens

<400> SEQUENCE: 70
ucucaagcug ugagucuaca aagggaagcc cuuucuguug ucuaaaagaa aagaaagugc      60
uucucuuugg uggguuacgg uuugaga                                          87

<210> SEQ ID NO 71
<211> LENGTH: 22
<212> TYPE: RNA
<213> ORGANISM: Homo sapiens

<400> SEQUENCE: 71
ucuggcuccg ugucuucacu cc                                               22

<210> SEQ ID NO 72
<211> LENGTH: 89
<212> TYPE: RNA
<213> ORGANISM: Homo sapiens

<400> SEQUENCE: 72
gccggcgccc gagcucuggc uccgugucuu cacucccgug cuuguccgag gagggaggga      60
gggacggggg cugugcuggg gcagcugga                                        89

<210> SEQ ID NO 73
```

```
<211> LENGTH: 87
<212> TYPE: RNA
<213> ORGANISM: Homo sapiens

<400> SEQUENCE: 73
ucucaagcug ugggucugca aagggaagcc cuuucuguug ucuaaaagaa gagaaagcgc    60
uucccuuugc uggauuacgg uuugaga                                       87

<210> SEQ ID NO 74
<211> LENGTH: 87
<212> TYPE: RNA
<213> ORGANISM: Homo sapiens

<400> SEQUENCE: 74
ucucaagcug ugagucuaca aagggaagcc cuuucuguug ucuaaaagaa agaaagugc    60 uucucuuugg uggguuacgg uuugaga                                       87

<210> SEQ ID NO 75
<211> LENGTH: 22
<212> TYPE: RNA
<213> ORGANISM: Homo sapiens

<400> SEQUENCE: 75
cucuagaggg aagcacuuuc ug                                            22

<210> SEQ ID NO 76
<211> LENGTH: 65
<212> TYPE: RNA
<213> ORGANISM: Homo sapiens

<400> SEQUENCE: 76
gugacccucu agagggaagc acuuucuguu gaaagaaaag aacaugcauc cuuucagagg    60
guuac                                                               65

<210> SEQ ID NO 77
<211> LENGTH: 85
<212> TYPE: RNA
<213> ORGANISM: Homo sapiens

<400> SEQUENCE: 77
cucaggcugu gacccucuag agggaagcac uuucuguugc uugaaagaag agaaagcgcu    60
uccuuuuaga ggauuacucu uugag                                         85

<210> SEQ ID NO 78
<211> LENGTH: 22
<212> TYPE: RNA
<213> ORGANISM: Homo sapiens

<400> SEQUENCE: 78
uaacacuguc ugguaaagau gg                                            22

<210> SEQ ID NO 79
<211> LENGTH: 95
<212> TYPE: RNA
<213> ORGANISM: Homo sapiens

<400> SEQUENCE: 79
cggccggccc uggguccauc uuccaguaca guguuggaug gucuaauugu gaagcccua    60 acacugucug guaaagaugg cucccgggug gguuc                              95

<210> SEQ ID NO 80
```

```
<211> LENGTH: 22
<212> TYPE: RNA
<213> ORGANISM: Homo sapiens

<400> SEQUENCE: 80
gaaggcgcuu cccuuuagag cg                                              22

<210> SEQ ID NO 81
<211> LENGTH: 85
<212> TYPE: RNA
<213> ORGANISM: Homo sapiens

<400> SEQUENCE: 81
cucaagcugu gacucuccag agggaugcac uuucucuuau gugaaaaaaa agaaggcgcu     60
ucccuuuaga gcguuacggu uggg                                            85

<210> SEQ ID NO 82
<211> LENGTH: 22
<212> TYPE: RNA
<213> ORGANISM: Homo sapiens

<400> SEQUENCE: 82
uucuccaaaa gggagcacuu uc                                              22

<210> SEQ ID NO 83
<211> LENGTH: 84
<212> TYPE: RNA
<213> ORGANISM: Homo sapiens

<400> SEQUENCE: 83
ucucaugcag ucauucucca aagggagca cuuucuguuu gaaagaaaac aaagugccuc      60
cuuuuagagu guuacuguuu gaga                                            84

<210> SEQ ID NO 84
<211> LENGTH: 21
<212> TYPE: RNA
<213> ORGANISM: Homo sapiens

<400> SEQUENCE: 84
caaagcgcuu cccuuuggag c                                               21

<210> SEQ ID NO 85
<211> LENGTH: 87
<212> TYPE: RNA
<213> ORGANISM: Homo sapiens

<400> SEQUENCE: 85
ucccaugcug ugacccucua gagggaagca cuuucuguug ucugaaagaa accaaagcgc     60
uucccuuugg agcguuacgg uuugaga                                         87

<210> SEQ ID NO 86
<211> LENGTH: 22
<212> TYPE: RNA
<213> ORGANISM: Homo sapiens

<400> SEQUENCE: 86
aagugcuguc auagcugagg uc                                              22

<210> SEQ ID NO 87
<211> LENGTH: 84
<212> TYPE: RNA
<213> ORGANISM: Homo sapiens
```

-continued

```
<400> SEQUENCE: 87
ucucagucug uggcacucag ccuugagggc acuuucuggu gccagaauga aagugcuguc    60
auagcugagg uccaaugacu gagg                                          84

<210> SEQ ID NO 88
<211> LENGTH: 98
<212> TYPE: RNA
<213> ORGANISM: Homo sapiens

<400> SEQUENCE: 88
gguacuucuc agucgugggc acucagccuu gagggcacuu ucggugcca gaaugaaagu    60 gcugucauag cugaggucca augacugagg cgagcacc                           98

<210> SEQ ID NO 89
<211> LENGTH: 23
<212> TYPE: RNA
<213> ORGANISM: Homo sapiens

<400> SEQUENCE: 89
caaagugccu cccuuuagag ugu                                           23

<210> SEQ ID NO 90
<211> LENGTH: 88
<212> TYPE: RNA
<213> ORGANISM: Homo sapiens

<400> SEQUENCE: 90
ucccaugcug ugacccucca aagggaagcg cuuucuguuu guuucucuu aaacaaagug    60 ccucccuuua gaguguuacc guuuggga                                      88

<210> SEQ ID NO 91
<211> LENGTH: 24
<212> TYPE: RNA
<213> ORGANISM: Homo sapiens

<400> SEQUENCE: 91
cucuagaggg aagcgcuuuc uguu                                          24

<210> SEQ ID NO 92
<211> LENGTH: 88
<212> TYPE: RNA
<213> ORGANISM: Homo sapiens

<400> SEQUENCE: 92
ucucaggcug ugacccucua gagggaagcg cuuucuguug gcuaaaagaa aagaaagcgc    60
uucccuucag aguguuaacg cuuugaga                                      88

<210> SEQ ID NO 93
<211> LENGTH: 22
<212> TYPE: RNA
<213> ORGANISM: Homo sapiens

<400> SEQUENCE: 93
ccucuagaug gaagcacugu cu                                            22

<210> SEQ ID NO 94
<211> LENGTH: 95
<212> TYPE: RNA
<213> ORGANISM: Homo sapiens

<400> SEQUENCE: 94
```

```
gaagaucuca ggcagugacc cucuagaugg aagcacuguc uguugcuaa gaaaagaucg    60 ugcauccuuu uagaguguua cuguuugaga aaauc                              95

<210> SEQ ID NO 95
<211> LENGTH: 24
<212> TYPE: RNA
<213> ORGANISM: Homo sapiens

<400> SEQUENCE: 95
guccaguuuu cccaggaauc ccuu                                          24

<210> SEQ ID NO 96
<211> LENGTH: 88
<212> TYPE: RNA
<213> ORGANISM: Homo sapiens

<400> SEQUENCE: 96
caccuugucc ucacggucca guuucccag gaaucccuua gaugcuaaga uggggauucc    60
uggaaauacu guucuugagg ucaugguu                                      88

<210> SEQ ID NO 97
<211> LENGTH: 22
<212> TYPE: RNA
<213> ORGANISM: Homo sapiens

<400> SEQUENCE: 97
uagcagcacg uaaauauugg cg                                            22

<210> SEQ ID NO 98
<211> LENGTH: 89
<212> TYPE: RNA
<213> ORGANISM: Homo sapiens

<400> SEQUENCE: 98
gucagcagug ccuuagcagc acguaaauau uggcguuaag auucuaaaau uaucuccagu    60
auuaacugug cugcugaagu aagguugac                                     89

<210> SEQ ID NO 99
<211> LENGTH: 81
<212> TYPE: RNA
<213> ORGANISM: Homo sapiens

<400> SEQUENCE: 99
guuccacucu agcagcacgu aaauauuggc guagugaaau auauuaaaa caccaauauu    60 acugugcugc uuuaguguga c                                             81

<210> SEQ ID NO 100
<211> LENGTH: 21
<212> TYPE: RNA
<213> ORGANISM: Homo sapiens

<400> SEQUENCE: 100
ucguaccgug aguaauaaug c                                             21

<210> SEQ ID NO 101
<211> LENGTH: 85
<212> TYPE: RNA
<213> ORGANISM: Homo sapiens

<400> SEQUENCE: 101
cgcuggcgac gggacauuau uacuuuuggu acgcgcugug acacuucaaa cucguaccgu    60
```

-continued

| gaguaauaau gcgccgucca cggca | 85 |

<210> SEQ ID NO 102
<211> LENGTH: 20
<212> TYPE: RNA
<213> ORGANISM: Homo sapiens

<400> SEQUENCE: 102

| guccgcucgg cgguggccca | 20 |

<210> SEQ ID NO 103
<211> LENGTH: 95
<212> TYPE: RNA
<213> ORGANISM: Homo sapiens

<400> SEQUENCE: 103

| gucgaggccg uggcccggaa guggucgggg ccgcugcggg cggaagggcg ccugugcuuc | 60 |
| guccgcucgg cgguggccca gccaggcccg cggga | 95 |

<210> SEQ ID NO 104
<211> LENGTH: 20
<212> TYPE: RNA
<213> ORGANISM: Homo sapiens

<400> SEQUENCE: 104

| agagguauag ggcaugggaa | 20 |

<210> SEQ ID NO 105
<211> LENGTH: 110
<212> TYPE: RNA
<213> ORGANISM: Homo sapiens

<400> SEQUENCE: 105

| cgccucagag ccgcccgccg uuccuuuuuc cuaugcauau acuucuuuga ggaucuggcc | 60 |
| uaaagaggua uagggcaugg gaaaacgggg cggucgdguc cuccccagcg | 110 |

<210> SEQ ID NO 106
<211> LENGTH: 22
<212> TYPE: RNA
<213> ORGANISM: Homo sapiens

<400> SEQUENCE: 106

| gaaagcgcuu cccuuugcug ga | 22 |

<210> SEQ ID NO 107
<211> LENGTH: 21
<212> TYPE: RNA
<213> ORGANISM: Homo sapiens

<400> SEQUENCE: 107

| aaagcgcuuc ccuucagagu g | 21 |

<210> SEQ ID NO 108
<211> LENGTH: 83
<212> TYPE: RNA
<213> ORGANISM: Homo sapiens

<400> SEQUENCE: 108

| ucucaugcag ucauucucca aaagaaagca cuuucuguug ucugaaagca gagugccuuc | 60 |
| uuuuggagcg uuacuguuug aga | 83 |

<210> SEQ ID NO 109

```
<211> LENGTH: 83
<212> TYPE: RNA
<213> ORGANISM: Homo sapiens

<400> SEQUENCE: 109
ucucaugcag ucauucucca aaagaaagca cuuucuguug ucugaaagca gagugccuuc      60
uuuuggagcg uuacuguuug aga                                             83

<210> SEQ ID NO 110
<211> LENGTH: 21
<212> TYPE: RNA
<213> ORGANISM: Homo sapiens

<400> SEQUENCE: 110
gaaggcgcuu cccuuuggag u                                               21
```

METHODS AND COMPOSITIONS FOR DIAGNOSING COMPLICATIONS OF PREGNANCY

CROSS-REFERENCE TO RELATED PATENT APPLICATIONS

This application is the U.S. National Phase of PCT/IL2009/000101, filed Jan. 26, 2009, which claims priority from U.S. Provisional Application Nos. 61/023,859, filed Jan. 27, 2008 and 61/040,671, filed Mar. 30, 2008, all of which are incorporated herein by reference in entirety.

FIELD OF THE INVENTION

The invention relates to methods and compositions for identifying subjects at risk of developing a complication of pregnancy, such as preeclampsia or preterm labor. The compositions are microRNAs and associated nucleic acids.

BACKGROUND OF THE INVENTION

Circulating nucleic acids (CNAs) in body fluids offer unique opportunities for early diagnosis of clinical conditions. Specific clinical biomarkers have the potential to revolutionize diagnosis and treatment of various medical conditions, such as abnormal pregnancies. The challenge of diverse biomedical research fields has been to identify biomarkers in body fluids, such as serum. In recent years it has become clear that both cell-free DNA and mRNA are present in serum, as well as in other body fluids, and represent potential biomarkers. However, monitoring the typically small amounts of these CNAs in body fluids requires sensitive detection methods, which are not currently clinically applicable.

microRNAs (miRNAs, miRs) have emerged as an important novel class of regulatory RNA, which has profound impact on a wide array of biological processes. These small (typically 17-24 nucleotides long) non-coding RNA molecules can modulate protein expression patterns by promoting RNA degradation, inhibiting mRNA translation, and also affecting gene transcription. miRs play pivotal roles in diverse processes such as development and differentiation, control of cell proliferation, stress response and metabolism. There are currently about 850 known human miRs.

Preeclampsia, complicating 3-5% of pregnancies, is associated with substantial risks for both the mother and the fetus. Although many theories exist for the etiology and pathogenesis of preeclampsia, its direct etiology remains unidentified. There has been little progress in the treatment of this disorder; the cure remains delivery of the fetus and removal of the placenta.

Effective management strategies for identifying and treating preterm labor are required to prevent preterm birth. Early births resulting from preterm labor result in a heavy burden of infant mortality and morbidity. Preterm birth is a factor in three-quarters of neonatal mortality and one-half of long-term neurologic impairment in children.

Early detection and management of preterm labor helps to prevent preterm birth and its potential neonatal sequelae, which include respiratory distress syndrome, sepsis, intraventricular hemorrhage, necrotizing enterocolitis, patent ductus arteriosus, and hyperbilirubinemia; however, widespread treatment of women with signs and symptoms of preterm labor has not significantly reduced the prevalence of preterm birth, underscoring the need to improve current methods for detecting preterm labor.

There is an unmet need for a reliable method for identifying subjects at risk of developing a complication of pregnancy, such as preeclampsia or preterm labor.

SUMMARY OF THE INVENTION

The present invention demonstrates for the first time that circulating microRNAs are novel serum markers with high stability and signature robustness.

The invention provides a method of determining a physiological condition in a subject, said method comprising detecting the level of a microRNA in a serum sample obtained from the subject, wherein a level of the microRNA different from a control is indicative of said physiological condition in said subject. According to some embodiments the physiological condition is a pregnancy-associated disorder. According to other embodiments the pregnancy-associated disorder is preeclampsia or preterm labor. According to some embodiments the detection of the microRNA level is determined by real-time PCR.

The invention further provides specific nucleic acid sequences that may be used for the identification and diagnosis of a complication of pregnancy, such as preeclampsia or preterm labor. According to some embodiments said nucleic acid sequences are selected from the group consisting of SEQ ID NOS: 1-110, a fragment thereof and a sequence having at least about 80% identity thereto.

The invention further provides a method for determining or aiding in the determination that a female subject is at risk of developing preeclampsia, comprising comparing the expression profile of a nucleic acid sequence selected from the group consisting of SEQ ID NOS: 5-17, a fragment thereof and a sequence having at least about 80% identity thereto in a biological sample from the subject to be assessed for risk of developing preeclampsia to a predetermined standard expression profile, wherein a significant difference in expression profile of said nucleic acid sequence in the sample as compared to the predetermined standard expression profile indicates that the subject is at risk of developing preeclampsia.

According to some embodiments, the predetermined standard expression profile corresponds to the expression profile of said nucleic acid sequence in a pregnant female subject who is not at risk of developing preeclampsia.

According to other embodiments, said biological sample is selected from the group consisting of bodily fluid and a tissue sample. According to some embodiments, said tissue is a fresh, frozen, fixed, wax-embedded or formalin fixed paraffin-embedded (FFPE) tissue.

According to one embodiment, the tissue sample is placenta sample or uterine myometrium sample. According to some embodiments, said bodily fluid sample is serum sample.

According to some embodiments, the method comprising determining the expression profile of at least two nucleic acid sequences. According to some embodiments the method further comprising combining one or more expression ratios. According to some embodiments, the expression levels are determined by a method selected from the group consisting of nucleic acid hybridization and nucleic acid amplification. According to some embodiments, the nucleic acid hybridization is performed using a solid-phase nucleic acid biochip array. According to certain embodiments, the nucleic acid hybridization is performed using in situ hybridization. According to other embodiments, the nucleic acid amplification method is real-time PCR. According to one embodiment, said real-time PCR is quantitative real-time PCR (qRT-PCR).

The invention further provides a method for detecting or monitoring a preterm labor in a female subject, comprising comparing the expression profile of a nucleic acid sequence selected from the group consisting of SEQ ID NOS: 18-25, a fragment thereof and a sequence having at least about 80% identity thereto in a biological sample from the subject to a predetermined standard expression profile, wherein a significant difference in the expression profile of said nucleic acid sequence in the sample as compared to the predetermined standard expression profile indicates that the subject is in preterm labor.

According to some embodiments, the predetermined standard expression profile corresponds to the expression profile of said nucleic acid sequence in a pregnant female subject who is not at risk of preterm labor.

The invention further provides a kit for determining if a subject female is at risk of developing preeclampsia, said kit comprises a probe comprising a nucleic acid sequence that is complementary to a sequence selected from the group consisting of SEQ ID NOS: 5-17, a fragment thereof and a sequence having at least about 80% identical thereto.

The invention further provides a kit for determining if a female subject is at risk of having a preterm labor, said kit comprising a probe comprising a nucleic acid sequence that is complementary to a sequence selected from the group consisting of SEQ ID NOS: 18-25, a fragment thereof and a sequence having at least about 80% identity thereto.

According to some embodiments, the kit further comprises forward and reverse primers.

These and other embodiments of the present invention will become apparent in conjunction with the figures, description and claims that follow.

BRIEF DESCRIPTION OF THE DRAWINGS

FIG. 1 shows differential expression of four microRNAs in the sera of pregnant vs. non-pregnant women. Expression level is specified as $50-C_T$, where $C_T$ is the cycle threshold of the PCR reaction. Results were normalized by subtracting the global microRNA expression in the sample (average $C_T$ of the 6 microRNAs chosen for normalization) from the $C_T$ level of each microRNA.
  A) Box plots comparing microRNA expression levels in the sera of 10 non-pregnant women (a), 10 women in first trimester (b), and 10 women in third trimester (c). The three placenta microRNAs (miR-527 (SEQ ID NO: 53), miR-520d-5p (SEQ ID NO: 69) and miR-526a (SEQ ID NO: 75)) are highly expressed in pregnant women and their expression level rises as the pregnancy progresses. hsa-let7d has similar expression levels in all groups.
  B) Box plots comparing microRNA miR-141 (SEQ ID NO: 78) and miR-149 (SEQ ID NO: 71) expression levels in the sera of the three groups.
  C) "Pregnancy classification" according to the levels of three microRNAs in the sera of pregnant vs. non-pregnant women. Discrimination of pregnant women from non-pregnant women based on microRNA expression levels in their sera. Circles represent non-pregnant women, triangles represent pregnant women and dots represent $3^{rd}$ trimester. The location of each symbol in the plot represents the collective expression of all three microRNAs in a given serum. The y axis indicates the expression level of mir 527, and the x axis indicates the average expression level of miR-520d-5p and miR-526a.

DETAILED DESCRIPTION OF THE INVENTION

Figure 1A:
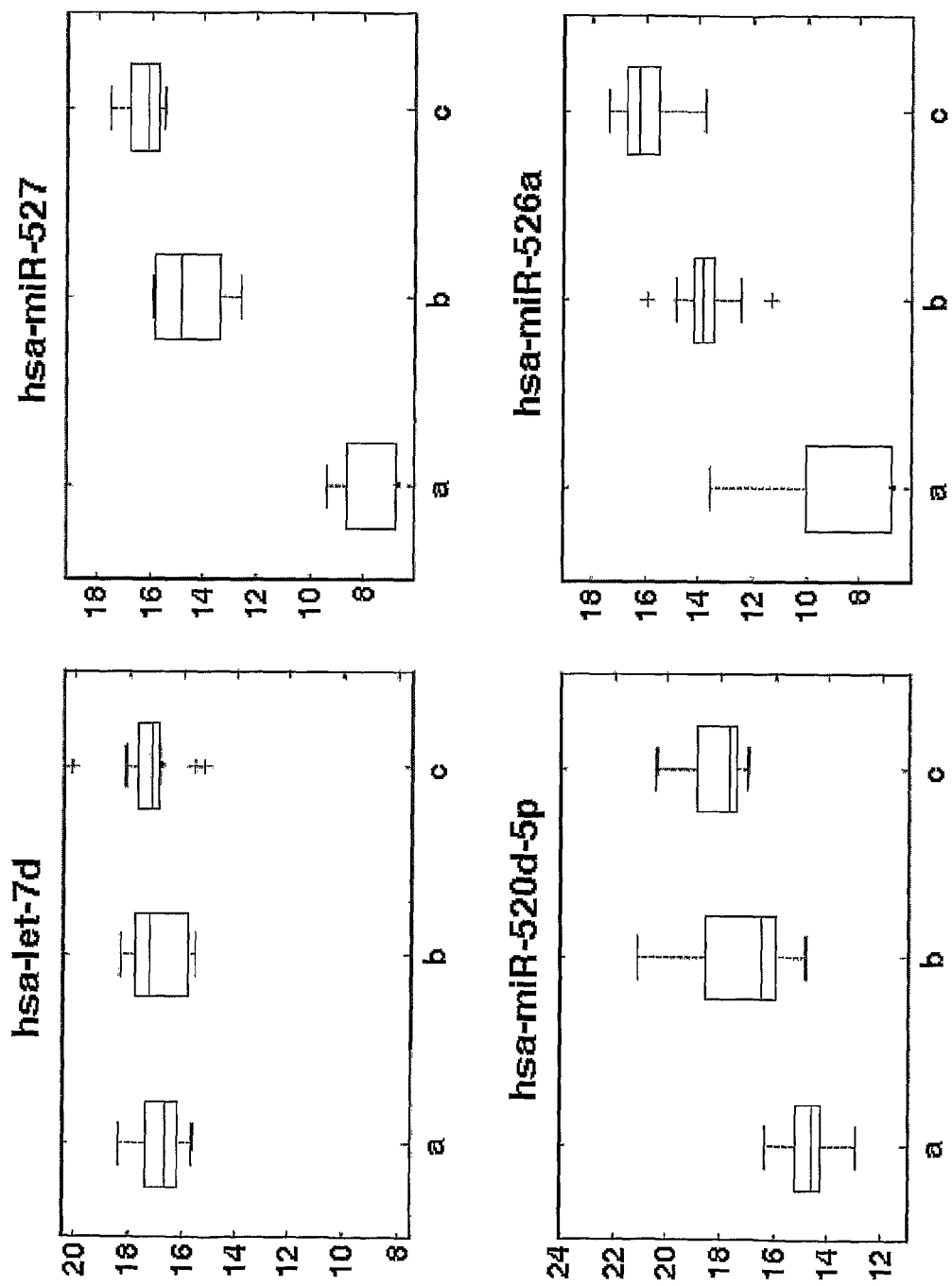
Figure 1B:
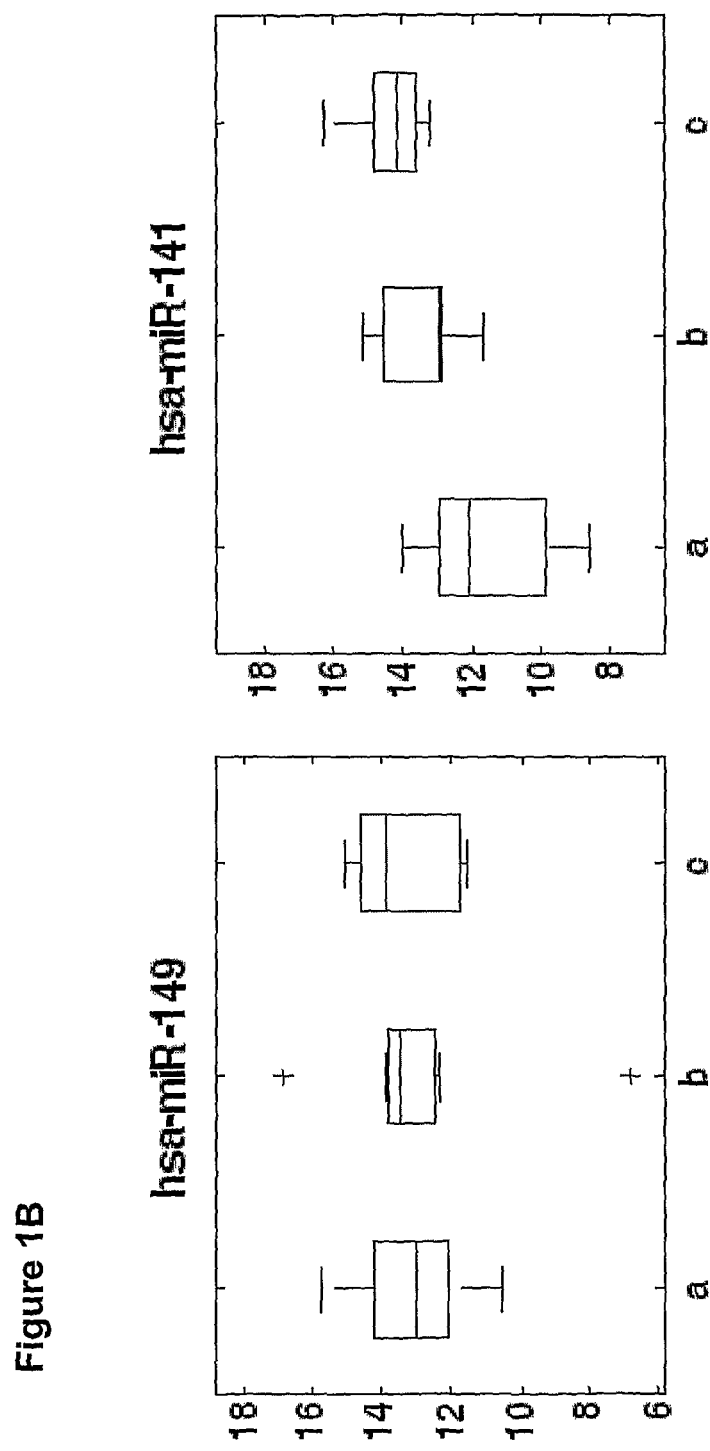

The invention is based on the discovery that specific nucleic acid sequences (SEQ ID NOS: 1-110) may be used for the identification and diagnosis of a complication of pregnancy, such as preeclampsia or preterm labor. The present invention demonstrates for the first time that serum levels of particular microRNAs may serve as diagnostic biomarkers for diverse physiological and pathological conditions. Moreover, the present invention demonstrates the ease and reliability of determining body fluid microRNA profiles and thus, paves the way for their wide application, both in the research laboratory and in the clinic. The methods of the present invention have high sensitivity and specificity.

Definitions

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9 and 7.0 are explicitly contemplated.

About

As used herein, the term "about" refers to +/−10%.

Antisense

The term "antisense," as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated.

Attached

"Attached" or "immobilized" as used herein to refer to a probe and a solid support may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

Biological Sample

"Biological sample" as used herein may mean a sample of biological tissue or fluid that comprises nucleic acids. Such samples include, but are not limited to, tissue or fluid isolated from animals. Biological samples may also include sections of tissues such as biopsy and autopsy samples, FFPE samples, frozen sections taken for histologic purposes, blood, plasma, serum, sputum, stool, tears, mucus, hair, and skin. Biological samples also include explants and primary and/or transformed cell cultures derived from animal or patient tissues. Biological samples may also be blood, a blood fraction, urine, effusions, ascitic fluid, saliva, cerebrospinal fluid, cervical secretions, vaginal secretions, endometrial secretions, gastrointestinal secretions, bronchial secretions, sputum, cell line, tissue sample, or secretions from the breast. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

Complement

"Complement" or "complementary" as used herein refer to a nucleic acid may mean Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

Ct

Ct signals represent the first cycle of PCR where amplification crosses a threshold (cycle threshold) of fluorescence. Accordingly, low values of Ct represent high abundance or expression levels of the microRNA. In some embodiments the PCR Ct signal is normalized such that the normalized Ct remains inversed from the expression level. In other embodiments the PCR Ct signal may be normalized and then inverted such that low normalized-inverted Ct represents low abundance or expression levels of the microRNA.

Detection

"Detection" may mean detecting the presence of a component in a sample. Detection may also mean detecting the absence of a component. Detection may also mean measuring the level of a component, either quantitatively or qualitatively.

Differential Expression

"Differential expression" may mean qualitative or quantitative differences in the temporal and/or cellular gene expression patterns within and among cells and tissue. Thus, a differentially expressed gene may qualitatively have its expression altered, including an activation or inactivation, in, e.g., normal versus disease tissue. Genes may be turned on or turned off in a particular state, relative to another state thus permitting comparison of two or more states. A qualitatively regulated gene may exhibit an expression pattern within a state or cell type which may be detectable by standard techniques. Some genes may be expressed in one state or cell type, but not in both. Alternatively, the difference in expression may be quantitative, e.g., in that expression is modulated, either up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, northern analysis, real-time PCR, and RNase protection.

Ectopic Pregnancy

An "ectopic pregnancy" refers to an abnormal pregnancy in which a fertilized egg has implanted outside the uterus. Although in most cases of ectopic pregnancy the egg settles in the fallopian tubes, this term also encompasses abnormal pregnancies where the fertilized egg is implanted in a woman's ovary, abdomen, or cervix.

Expression Profile

The term "expression profile" is used broadly to include a genomic expression profile, e.g., an expression profile of microRNAs. Profiles may be generated by any convenient means for determining a level of a nucleic acid sequence e.g. quantitative hybridization of microRNA, labeled microRNA, amplified microRNA, cRNA, etc., quantitative PCR, ELISA for quantitation, and the like, and allow the analysis of differential gene expression between two samples. A subject or patient sample, e.g., cells or a collection thereof, e.g., tissues, is assayed. Samples are collected by any convenient method, as known in the art. Nucleic acid sequences of interest are nucleic acid sequences that are found to be predictive, including the nucleic acid sequences provided above, where the expression profile may include expression data for 2, 5, 10, 20, 25, 50, 100 or more of, including all of the listed nucleic acid sequences. According to some embodiments, the term "expression profile" means measuring the abundance of the nucleic acid sequences in the measured samples.

Expression Ratio

"Expression ratio" as used herein refers to relative expression levels of two or more nucleic acids as determined by detecting the relative expression levels of the corresponding nucleic acids in a biological sample.

Fragment

"Fragment" is used herein to indicate a non-full length part of a nucleic acid. Thus, a fragment is itself also a nucleic acid.

Gene

"Gene" used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

Groove Binder/Minor Groove Binder (MGB)

"Groove binder" and/or "minor groove binder" may be used interchangeably and refer to small molecules that fit into the minor groove of double-stranded DNA, typically in a sequence-specific manner. Minor groove binders may be long, flat molecules that can adopt a crescent-like shape and thus, fit snugly into the minor groove of a double helix, often displacing water. Minor groove binding molecules may typically comprise several aromatic rings connected by bonds with torsional freedom such as furan, benzene, or pyrrole rings. Minor groove binders may be antibiotics such as netropsin, distamycin, berenil, pentamidine and other aromatic diamidines, Hoechst 33258, SN 6999, aureolic antitumor drugs such as chromomycin and mithramycin, CC-1065, dihydrocyclopyrroloindole tripeptide ($DPI_3$), 1,2-dihydro-(3H)-pyrrolo[3,2-e]indole-7-carboxylate ($CDPI_3$), and related compounds and analogues, including those described in Nucleic Acids in Chemistry and Biology, 2d ed., Blackburn and Gait, eds., Oxford University Press, 1996, and PCT Published Application No. WO 03/078450, the contents of which are incorporated herein by reference. A minor groove binder may be a component of a primer, a probe, a hybridization tag complement, or combinations thereof. Minor groove binders may increase the $T_m$ of the primer or a probe to which they are attached, allowing such primers or probes to effectively hybridize at higher temperatures.

Identity

"Identical" or "identity" as used herein in the context of two or more nucleic acids or polypeptide sequences may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

Label

"Label" as used herein may mean a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

Nucleic Acid

"Nucleic acid" or "oligonucleotide" or "polynucleotide" used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 542-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 438:685-689 (2005), Soutschek et al., Nature 432:173-178 (2004), and U.S. Patent Publication No. 20050107325, which are incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver and kidney. Mixtures of naturally occurring nucleic acids and analogs may be made; alternatively, mixtures of different nucleic acid analogs, and mixtures of naturally occurring nucleic acids and analogs may be made.

Pregnancy-Associated Disorder

The term "pregnancy-associated disorder" as used in this application, refers to any condition or disease that may affect a pregnant woman, the fetus the woman is carrying, or both the woman and the fetus. Such a condition or disease may manifest its symptoms during a limited time period, e.g., during pregnancy or delivery, or may last the entire life span of the fetus following its birth. Some examples of a pregnancy-associated disorder include preeclampsia, preterm labor, ectopic pregnancy, and fetal chromosomal abnormalities.

Preeclampsia

The term "preeclampsia" as used herein refers to a condition that occurs during pregnancy, the main symptom of which is various forms of high blood pressure often accompanied by the presence of proteins in the urine and edema (swelling). Preeclampsia, sometimes called toxemia of pregnancy, is related to a more serious disorder called "eclampsia," which is preeclampsia together with seizures. These conditions usually develop during the second half of pregnancy (after 20 weeks), though they may develop shortly after birth or before 20 weeks of pregnancy.

Preterm Labor

The term "preterm labor" or "premature labor" as used herein refers to the condition where labor that begins more than three weeks before the full gestation period of about 40 weeks, which often leads to premature birth if not treated.

Probe

"Probe" as used herein may mean an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

Reference Expression Profile

As used herein, the phrase "reference expression profile" or "predetermined standard expression profile" refers to a criterion expression value to which measured values are compared in order to determine the detection of a subject at risk of developing a complication of pregnancy. The reference expression profile may be based on the abundance of the nucleic acids, or may be based on a combined metric score thereof.

Stringent Hybridization Conditions

"Stringent hybridization conditions" used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

Substantially Complementary

"Substantially complementary" used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

Substantially Identical

"Substantially identical" used herein may mean that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

Subject

As used herein, the term "subject" refers to a mammal, including both human and other mammals. The methods of the present invention are preferably applied to human subjects.

Target Nucleic Acid

"Target nucleic acid" as used herein may mean a nucleic acid or variant thereof that may be bound by another nucleic acid. A target nucleic acid may be a DNA sequence. The target nucleic acid may be an RNA. The target nucleic acid may comprise a mRNA, tRNA, snRNA, siRNA or Piwi-interacting RNA, or a pri-miRNA, pre-miRNA, miRNA, or anti-miRNA. The target nucleic acid may comprise a target miRNA binding site or a variant thereof. One or more probes may bind the target nucleic acid. The target binding site may comprise 5-100 or 10-60 nucleotides. The target binding site may comprise a total of 5, 6, 7, 8, 9, 10, 11, 12, 13, 14, 15, 16, 17, 18, 19, 20, 21, 22, 23, 24, 25, 26, 27, 28, 29, 30-40, 40-50, 50-60, 61, 62 or 63 nucleotides. The target site sequence may comprise at least 5 nucleotides of the sequence of a target miRNA binding site disclosed in U.S. patent application Ser. Nos. 11/384,049, 11/418,870 or 11/429,720, the contents of which are incorporated herein.

Tissue Sample

As used herein, a tissue sample is tissue obtained from a tissue biopsy using methods well known to those of ordinary skill in the related medical arts. Methods for obtaining the sample from the biopsy include gross apportioning of a mass, microdissection, laser-based microdissection, or other art-known cell-separation methods.

Variant

"Variant" used herein to refer to a nucleic acid may mean (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

Wild Type

As used herein, the term "wild type" sequence refers to a coding, non-coding or interface sequence is an allelic form of sequence that performs the natural or normal function for that sequence. Wild type sequences include multiple allelic forms of a cognate sequence, for example, multiple alleles of a wild type sequence may encode silent or conservative changes to the protein sequence that a coding sequence encodes.

Considering the central role of microRNAs in development and disease, the present invention highlights the medically relevant potential of determining microRNA levels in serum and other body fluids. Thus, microRNAs are a new class of CNAs that promise to serve as useful clinical biomarker.

microRNA Processing

A gene coding for a miRNA may be transcribed leading to production of an miRNA precursor known as the pri-miRNA. The pri-miRNA may be part of a polycistronic RNA comprising multiple pri-miRNAs. The pri-miRNA may form a hairpin with a stem and loop. The stem may comprise mismatched bases.

The hairpin structure of the pri-miRNA may be recognized by Drosha, which is an RNase III endonuclease. Drosha may recognize terminal loops in the pri-miRNA and cleave approximately two helical turns into the stem to produce a 60-70 nt precursor known as the pre-miRNA. Drosha may cleave the pri-miRNA with a staggered cut typical of RNase III endonucleases yielding a pre-miRNA stem loop with a 5' phosphate and ~2 nucleotide 3' overhang. Approximately one helical turn of stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an RNase III endonuclease. Dicer may recognize the double-stranded stem of the pre-miRNA. Dicer may also recognize the 5' phosphate and 3' overhang at the base of the stem loop. Dicer may cleave off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. mRNA* sequences may be found in libraries of cloned miRNAs but typically at lower frequency than the miRNAs.

Although initially present as a double-stranded species with miRNA*, the miRNA may eventually become incorporated as a single-stranded RNA into a ribonucleoprotein complex known as the RNA-induced silencing complex (RISC). Various proteins can form the RISC, which can lead to variability in specifity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-7 of the miRNA. Only one case has been reported in animals where the interaction between the miRNA and its target was along the entire length of the miRNA. This was shown for mir-196 and Hox B8 and it was further shown that mir-196 mediates the cleavage of the Hox B8 mRNA (Yekta et al 2004, Science 304-594). Otherwise, such interactions are known only in plants (Bartel & Bartel 2003, Plant Physiol 132-709).

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke et al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RIS Cs provides the most efficient translational inhibition.

MiRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

Nucleic Acid

Nucleic acids are provided herein. The nucleic acid may comprise the sequence of SEQ ID NOS: 1-110 or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from 10 to 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a synthetic gene described herein. The nucleic acid may be synthesized as a single strand molecule and hybridized to a substantially complementary nucleic acid to form a duplex. The nucleic acid may be introduced to a cell, tissue or organ in a single- or double-stranded form or capable of being expressed by a synthetic gene using methods well known to those skilled in the art, including as described in U.S. Pat. No. 6,506,559 which is incorporated by reference.

Nucleic Acid Complexes

The nucleic acid may further comprise one or more of the following: a peptide, a protein, a RNA-DNA hybrid, an antibody, an antibody fragment, a Fab fragment, and an aptamer.

Pri-miRNA

The nucleic acid may comprise a sequence of a pri-miRNA or a variant thereof. The pri-miRNA sequence may comprise from 45-30,000, 50-25,000,100-20,000, 1,000-1,500 or 80-100 nucleotides. The sequence of the pri-miRNA may comprise a pre-miRNA, miRNA and miRNA*, as set forth herein, and variants thereof. The sequence of the pri-miRNA may comprise the sequence of SEQ ID NOS: 1-110 or variants thereof.

The pri-miRNA may form a hairpin structure. The hairpin may comprise a first and second nucleic acid sequence that are substantially complimentary. The first and second nucleic acid sequence may be from 37-50 nucleotides. The first and second nucleic acid sequence may be separated by a third sequence of from 8-12 nucleotides. The hairpin structure may have a free energy less than −25 Kcal/mole as calculated by the Vienna algorithm with default parameters, as described in Hofacker et al., Monatshefte f. Chemie 125: 167-188 (1994), the contents of which are incorporated herein. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

Pre-miRNA

The nucleic acid may also comprise a sequence of a pre-miRNA or a variant thereof. The pre-miRNA sequence may comprise from 45-90, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 1-110 or variants thereof.

MiRNA

The nucleic acid may also comprise a sequence of a miRNA (including miRNA*) or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise the sequence of SEQ ID NOS: 1-25, 51-110 or variants thereof.

Anti-miRNA

The nucleic acid may also comprise a sequence of an anti-miRNA that is capable of blocking the activity of a miRNA or miRNA*, such as by binding to the pri-miRNA, pre-miRNA, miRNA or miRNA* (e.g. antisense or RNA silencing), or by binding to the target binding site. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the anti-miRNA may comprise (a) at least 5 nucleotides that are substantially identical or complimentary to the 5' of a miRNA and at least 5-12 nucleotides that are substantially complimentary to the flanking regions of the target site from the 5' end of the miRNA, or (b) at least 5-12 nucleotides that are substantially identical or complimentary to the 3' of a miRNA and at least 5 nucleotide that are substantially complimentary to the flanking region of the target site from the 3' end of the miRNA. The sequence of the anti-miRNA may comprise the compliment of SEQ ID NOS: 1-110 or variants thereof.

Binding Site of Target

The nucleic acid may also comprise a sequence of a target microRNA binding site, or a variant thereof. The target site sequence may comprise a total of 5-100 or 10-60 nucleotides. The target site sequence may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62 or 63 nucleotides. The target site sequence may comprise at least 5 nucleotides of the sequence of SEQ ID NOS: 1-110.

Synthetic Gene

A synthetic gene is also provided comprising a nucleic acid described herein operably linked to a transcriptional and/or translational regulatory sequence. The synthetic gene may be capable of modifying the expression of a target gene with a binding site for a nucleic acid described herein. Expression of the target gene may be modified in a cell, tissue or organ. The synthetic gene may be synthesized or derived from naturally-occurring genes by standard recombinant techniques. The synthetic gene may also comprise terminators at the 3'-end of the transcriptional unit of the synthetic gene sequence. The synthetic gene may also comprise a selectable marker.

Vector

A vector is also provided comprising a synthetic gene described herein. The vector may be an expression vector. An expression vector may comprise additional elements. For example, the expression vector may have two replication systems allowing it to be maintained in two organisms, e.g., in one host cell for expression and in a second host cell (e.g., bacteria) for cloning and amplification. For integrating expression vectors, the expression vector may contain at least one sequence homologous to the host cell genome, and preferably two homologous sequences which flank the expression construct. The integrating vector may be directed to a specific locus in the host cell by selecting the appropriate homologous sequence for inclusion in the vector. The vector may also comprise a selectable marker gene to allow the selection of transformed host cells.

Host Cell

A host cell is also provided comprising a vector, synthetic gene or nucleic acid described herein. The cell may be a bacterial, fungal, plant, insect or animal cell. For example, the host cell line may be DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte) and 293 (human kidney). Host cell lines may be available from commercial services, the American Tissue Culture Collection or from published literature.

Probes

A probe is provided herein. A probe may comprise a nucleic acid. The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may comprise a nucleic acid of 18-25 nucleotides.

A probe may be capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. A probe may be single stranded or partially single and partially double stranded. The strandedness of the probe is dictated by the structure, composition, and properties of the target sequence. Probes may be directly labeled or indirectly labeled.

Test Probe

The probe may be a test probe. The test probe may comprise a nucleic acid sequence that is complementary to a miRNA, a miRNA*, a pre-miRNA, or a pri-miRNA. The sequence of the test probe may be selected from SEQ ID NOS: 1-110 or fragment thereof.

Linker Sequences

The probe may further comprise a linker. The linker may be 10-60 nucleotides in length. The linker may be 20-27 nucleotides in length. The linker may be of sufficient length to allow the probe to be a total length of 45-60 nucleotides. The linker may not be capable of forming a stable secondary structure, may not be capable of folding on itself, or may not be capable of folding on a non-linker portion of a nucleic acid contained in the probe. The sequence of the linker may not appear in the genome of the animal from which the probe non-linker nucleic acid is derived.

Reverse Transcription

Target sequences of a cDNA may be generated by reverse transcription of the target RNA. Methods for generating cDNA may be reverse transcribing polyadenylated RNA or alternatively, RNA with a ligated adaptor sequence.

Reverse Transcription using Adaptor Sequence Ligated to RNA

The RNA may be ligated to an adapter sequence prior to reverse transcription. A ligation reaction may be performed by T4 RNA ligase to ligate an adaptor sequence at the 3' end of the RNA. Reverse transcription (RT) reaction may then be performed using a primer comprising a sequence that is complementary to the 3' end of the adaptor sequence.

Reverse Transcription using Polyadenylated Sequence Ligated to RNA

Polyadenylated RNA may be used in a reverse transcription (RT) reaction using a poly(T) primer comprising a 5' adaptor sequence.

RT-PCR of RNA

The reverse transcript of the RNA may be amplified by real time PCR, using a specific forward primer comprising at least 15 nucleic acids complementary to the target nucleic acid and a 5' tail sequence; a reverse primer that is complementary to the 3' end of the adaptor sequence; and a probe comprising at least 8 nucleic acids complementary to the target nucleic acid. The probe may be partially complementary to the 5' end of the adaptor sequence.

PCR of Target Nucleic Acids

Methods of amplifying target nucleic acids are described herein. The amplification may be by a method comprising PCR. The first cycles of the PCR reaction may have an annealing temp of 56° C., 57° C., 58° C., 59° C., or 60° C. The first cycles may comprise 1-10 cycles. The remaining cycles of the PCR reaction may be 60° C. The remaining cycles may comprise 2-40 cycles. The annealing temperature may cause the PCR to be more sensitive. The PCR may generate longer products that can serve as higher stringency PCR templates.

Forward Primer

The PCR reaction may comprise a forward primer. The forward primer may comprise 15, 16, 17, 18, 19, 20, or 21 nucleotides identical to the target nucleic acid. The 3' end of the forward primer may be sensitive to differences in sequence between a target nucleic acid and a sibling nucleic acid.

The forward primer may also comprise a 5' overhanging tail. The 5' tail may increase the melting temperature of the forward primer. The sequence of the 5' tail may comprise a sequence that is non-identical to the genome of the animal from which the target nucleic acid is isolated. The sequence of the 5' tail may also be synthetic. The 5' tail may comprise 8, 9, 10, 11, 12, 13, 14, 15, or 16 nucleotides.

Reverse Primer

The PCR reaction may comprise a reverse primer. The reverse primer may be complementary to a target nucleic acid. The reverse primer may also comprise a sequence complementary to an adaptor sequence. The sequence complementary to an adaptor sequence may comprise 12-24 nucleotides.

Biochip

A biochip is also provided. The biochip may comprise a solid substrate comprising an attached probe or plurality of probes described herein. The probes may be capable of hybridizing to a target sequence under stringent hybridization conditions. The probes may be attached at spatially defined addresses on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as a flexible foam, including closed cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide.

The probe may also be attached to the solid support noncovalently. For example, biotinylated oligonucleotides can be made, which may bind to surfaces covalently coated with streptavidin, resulting in attachment. Alternatively, probes may be synthesized on the surface using techniques such as photopolymerization and photolithography.

Diagnostic

A method of diagnosis is also provided. The method comprises detecting a differential expression level of preeclampsia or preterm labor associated nucleic acid in a biological sample. The sample may be derived from a female patient. Diagnosis of preeclampsia or preterm labor in a female patient may allow for prognosis and selection of therapeutic strategy. The skilled artisan can make a diagnosis, a prognosis, or a prediction based on the findings.

Kits

A kit is also provided and may comprise a nucleic acid described herein together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein.

For example, the kit may be a kit for the amplification, detection, identification or quantification of a target nucleic acid sequence. The kit may comprise a poly (T) primer, a forward primer, a reverse primer, and a probe.

The following examples are presented in order to more fully illustrate some embodiments of the invention. They should, in no way be construed, however, as limiting the broad scope of the invention.

EXAMPLES

Example 1

Experimental Procedures

1. Study Population

The first study group included 20 pregnant women: 10 in the first trimester (6-12 weeks of gestational age) and 10 in the third trimester (34-41 weeks of gestational age) and from 10 control, age-matched non-pregnant women. Eligibility for the study was limited to normal uncomplicated singleton pregnancy with no known fetal malformation. All women provided written informed consent and the local institutional review board approved the study.

The second study group included women with preeclampsia that were delivered by cesarean section prior to onset of spontaneous delivery. The control group included women delivering by cesarean section prior to onset of spontaneous delivery with no clinical or laboratory evidence of hypertensive disorder of pregnancy. Spontaneous onset of labor was defined by regular painful contractions or cervical dilatation >=4 cm. Preeclampsia was defined based on elevated blood pressure (systolic>=140 mmHg or diastolic>=90 mmHg) and proteinuria (>=300 mg/24 h or >=1+dipstick) that appear after 20 weeks of gestation. Severe preeclampsia was defined as preeclampsia with one of the following: systolic blood pressure >=160 mmHg, diastolic blood pressure >=110 mmHg, proteinuria >=5 grams/24 h, the presence of headache, visual disturbance or persistent epigastric pain, seizures, oliguria, elevated creatinine levels, platelets count <100,000/uL, elevated liver enzymes, evidence of hemolysis, or fetal growth restriction according to local birthweight curves. Exclusion criteria included multiple gestations, women with chronic hypertension, gestational age <24 weeks, uncertain gestational age, or clinical or histological evidence of chorioamnionitis. The third study group included women with spontaneous preterm onset of delivery (<34 weeks of gestation), during active phase of delivery (>4 cm cervical dilatation and regular contractions) and control group of women delivering at term (women with suspected chorioamniotis were excluded). All women in the current study were delivered by cesarean section. All participants provided written informed consent and the local IRB committee approved the study.

2. Sampling of Body Fluids, Placenta and Myometrium

Prior to the onset of cesarean section, a blood sample (5 cc, in a sodium citrate containing test-tube), was taken. During cesarean section, after delivery of the infant, the placenta was manually removed. Full thickness samples (about 1 g each) were taken from the placenta at areas that macroscopically had no evidence of abruption or infarction. After delivery of the infant and removal of the placenta, a full thickness myometrial sample about 5×5 mm was taken from the superior edge of the transverse uterine incision with a curved Mayo-scissors. Both placental and myometrium samples were immediately frozen in liquid nitrogen and transferred for storage in a −70° C. refrigerator. Because previous studies have shown that there is a dramatic change in gene expression profile in the placenta during labor, all samples were taken from placentas of women undergoing cesarean section prior to the onset of labor.

Serum Samples 8 ml of blood was collected from each woman directly into serum collection tubes (Greiner Bio-one, VACUETTE® Serum Tubes 455071). The whole blood was allowed to stand for about 1 h at RT before being centrifuged at 1800 g for 10 minutes at RT. The resultant serum was aliquoted into eppendorf tubes and stored at −80° C.

Urine Samples

About 4 ml of urine was collected from each individual in a urine container. The urine was then aliquoted into eppendorf tubes and kept frozen at −80° C. until it was used for RNA extraction.

3. miR Microarray Platform

Custom microarrays were produced by printing DNA oligonucleotide probes representing 688 miRNAs [Sanger database, version 9.2 (miRBase: microRNA sequences, targets and gene nomenclature. Griffiths-Jones S, Grocock R J, van Dongen S, Bateman A, Enright A J. NAR, 2006, 34, Database Issue, D140-D144) and additional Rosetta genomics validated and predicted miRs]. Each probe carries up to 22-nt linker at the 3' end of the miRNA's complement sequence in addition to an amine group used to couple the probes to coated glass slides. 20 µM of each probe were dissolved in 2×SSC+ 0.0035% SDS and spotted in triplicate on Schott Nexterion® Slide E coated microarray slides using a Genomic Solutions® BioRobotics MicroGrid II according the MicroGrid manufacturer's directions. 64 negative control probes were designed using the sense sequences of different miRNAs. Two groups of positive control probes were designed to hybridize to miR microarray. Synthetic spikes small RNA were added to the RNA before labeling to verify the labeling efficiency and (2) probes for abundant small RNA (e.g. small nuclear RNAs (U43, U49, U24, Z30, U6, U48, U44), 5.8s and 5s ribosomal RNA) were spotted on the array to verify RNA quality. The slides were blocked in a solution containing 50 mM ethanolamine, 1M Tris (pH 9.0) and 0.1% SDS for 20 min at 50° C., then thoroughly rinsed with water and spun dry.

4. Cy-Dye Labeling of microRNA for miR Microarray 1.5-3.5 µg of total RNA was labeled by ligation of a RNA-linker p-rCrU-Cy-dye (Thomson et al., 2004, Nat Methods 1, 47-53) (Eurogentec) to the 3'-end with Cy3 or Cy5. The labeling reaction contained total RNA, spikes (20-0.1 fmoles), 500 ng RNA-linker-dye, 15% DMSO, 1× ligase buffer and 20 units of T4 RNA ligase (NEB) and proceeded at 4° C. for 1 hr followed by 1 hr at 37° C. The labeled RNA was mixed with 3× hybridization buffer (Ambion), heated to 95° C. for 3 mM and than added on top of the miR microarray. Slides were hybridize 12-16 hr, followed by two washes with 1×SSC and 0.2% SDS and a final wash with 0.1×SSC.

The array was scanned using an Agilent Microarray Scanner Bundle G2565BA (resolution of 10 µm at 100% power). The data was analyzed using SpotReader software.

5. RNA Extraction

RNA was extracted from frozen samples originated from placental tissue and myometrium. Total RNA from frozen tissues was extracted with the miRvana miRNA isolation kit (Ambion) according to the manufacturer's instructions. 100 ul serum or urine was incubated at 56° C. for 1 h with 0.65 mg/ml Proteinase K, (Sigma P2308). Two synthetic RNAs were spiked-in as controls before acid phenol:chloroform extraction and then RNA was ETOH precipitated ON at −20° C. Next, DNase treatment was performed to eliminate residual DNA fragments. Finally, after a second acid phenol: chloroform extraction, the pellet was re-suspended in DDW and two additional synthetic RNAs are spiked-in as controls.

6. miR qRT-PCR Platform

RNA was subjected to polyadenylation reaction as described previously (Rui Shi and Vincent L. Chiang. Facile means for quantifying microRNA expression by real-time PCR. BioTechniques (2005) 39:519-525). Briefly, RNA was incubated in the presence of poly (A) polymerase (PAP) (Takara-2180A), PNK buffer (NEB) MnCl$_2$, and ATP for 1 h at 37° C. Then, using an oligodT primer harboring a consensus sequence (complementary to the reverse primer) reverse transcription was performed on total RNA, using SuperScript II RT (Invitrogen).

Next, the cDNA was amplified by real time PCR; this reaction contained a microRNA-specific forward primer, a TaqMan probe complementary to 8 nts of the 3' end of the specific microRNA sequence as well as to 12 nts of the polyA adaptor and to few bases (2-4) on the 5' of the oligodT tail; and universal reverse primer complementary to the 3' sequence of the oligo dT tail.

Example 2 microRNAs in Body Fluids Represent Novel Clinical Biomarkers

We have developed a protocol for extracting cell-free microRNAs from body fluids (see Example 1). Assessment of extracted microRNA levels was achieved using a proprietary qRT-PCR technique, which is highly sensitive. The qRT-PCR method detects specifically mature microRNA molecules, and allows discrimination between homologous microRNA family members that differ by a single nucleotide. The sensitivity and specificity of this qRT-PCR method is demonstrated by our ability to detect a few molecules of microRNA present in a non-relevant RNA background. Such high sensitivity makes it possible to use qRT-PCR to monitor the minute amount of microRNA present in cell-free body fluids.

In order for microRNAs in serum to be useful biomarkers they must be stable for reasonable periods of time to allow for routine processing of clinical samples. We found that the expression levels of different microRNAs in unfrozen serum do not change substantially over a 4 hour period at room temperature, and also are not affected by twice freezing and re-thawing of samples (data not shown). Thus, microRNAs in serum are sufficiently robust to serve as potential clinical biomarkers. Additionally, we observed that these microRNAs are expressed similarly in serum samples taken from different healthy individuals. Therefore, we anticipate that differences in expression between individuals of only particular microRNAs could be used to indicate clinical conditions. Notably, using our extraction and qRT-PCR methods we established that microRNAs are also present in other body fluids, such as urine, saliva, amniotic fluid and pleural fluid.

Finally, as a proof of concept, we investigated whether circulating microRNAs can be used to identify clinical conditions. It has been established that circulating maternal RNA contains placental embryonic RNA. We measured the levels of 28 microRNAs, including placenta-specific microRNAs, as well as broadly expressed microRNAs.

Figure 1C:
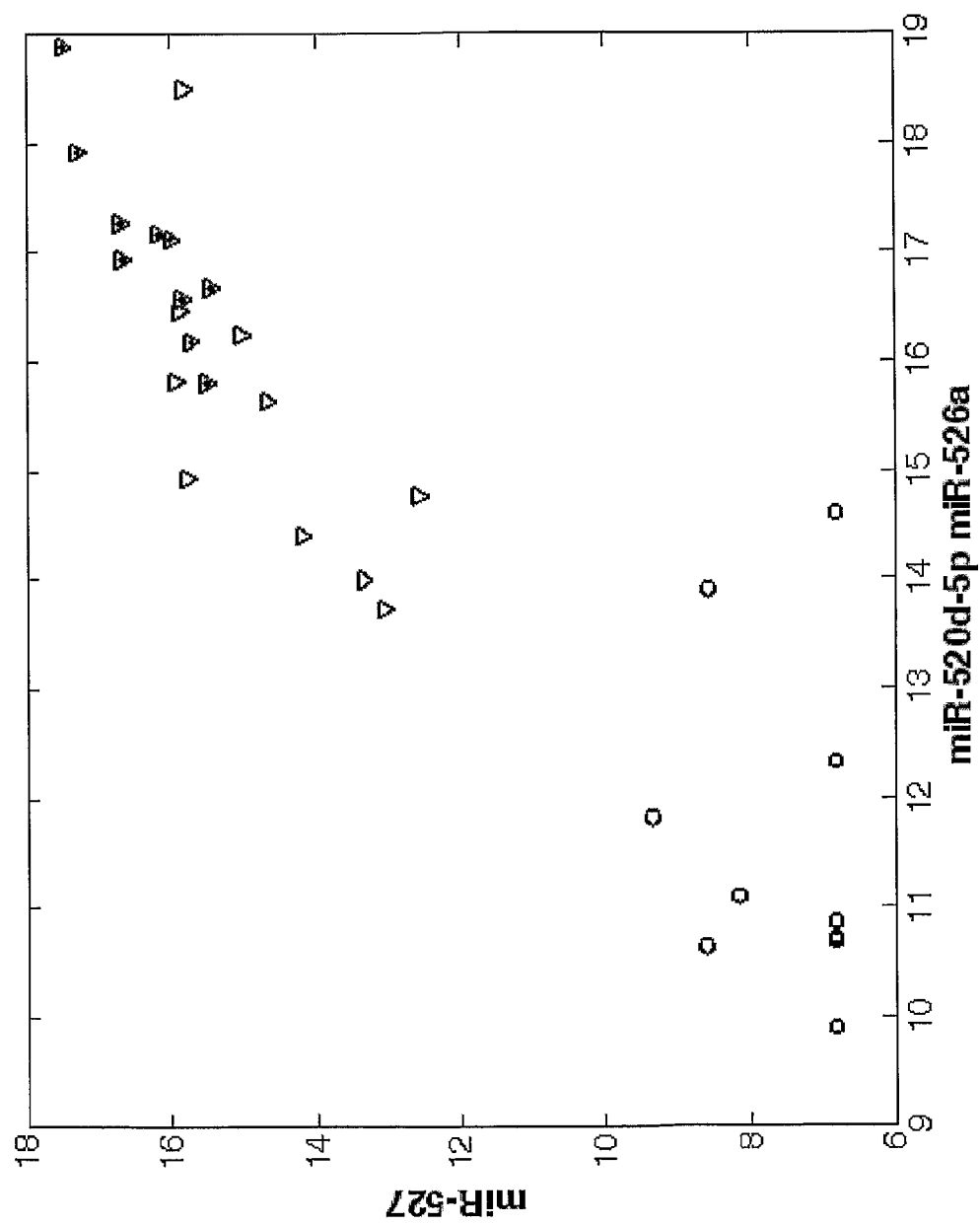
Figure 2:
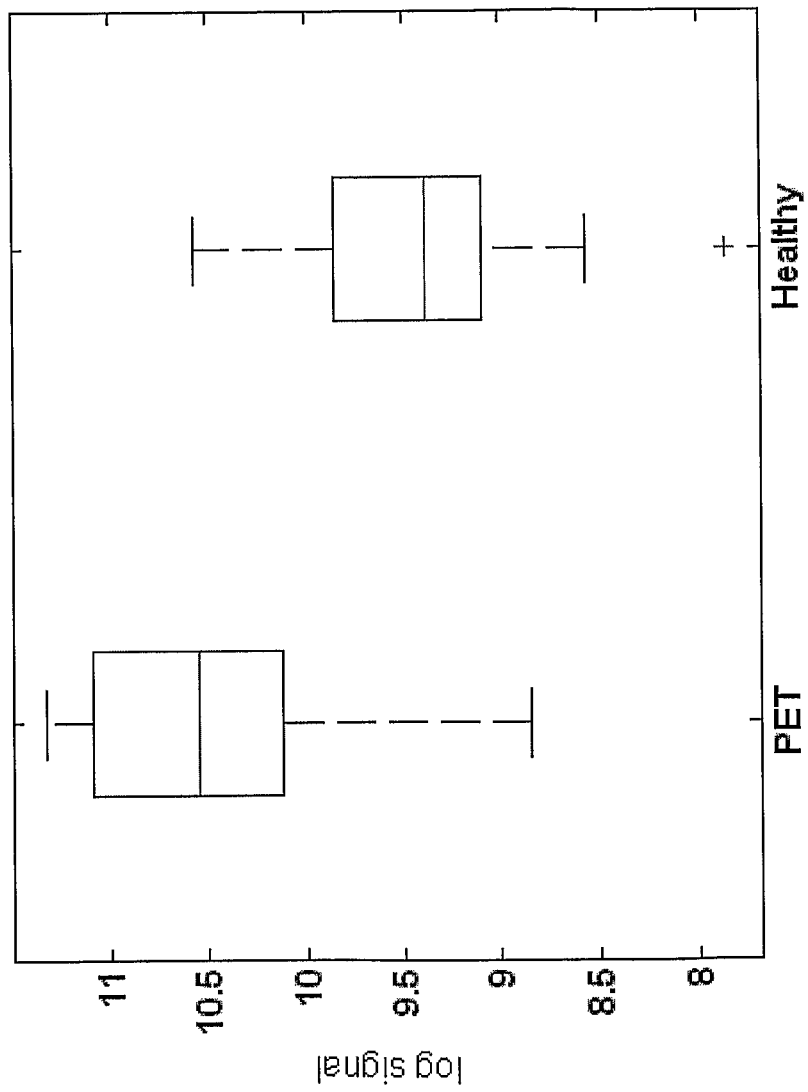
FIG. 2 shows differential expression of hsa-miR-31 (SEQ ID NO: 5) based on biochip array of placenta samples obtained from women with severe preeclampsia (PET) and healthy women underwent cesarean section prior to spontaneous onset of delivery (t-test p-value<0.015).
Figure 3:
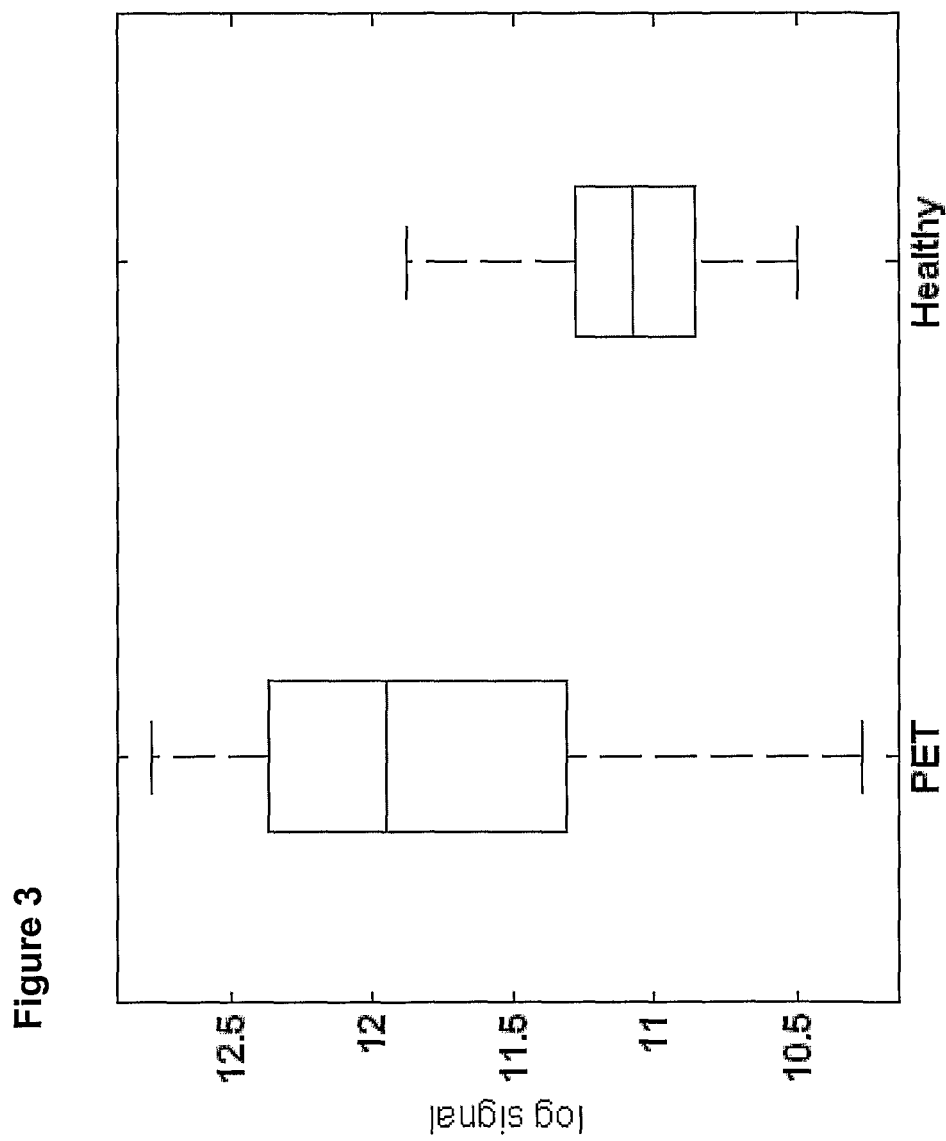
FIG. 3 shows differential expression of ambi-miR-7510 (SEQ ID NO: 6) based on biochip array of placenta samples obtained from women with severe preeclampsia (PET) and healthy women underwent cesarean section prior to spontaneous onset of delivery (t-test p-value<0.015).
Figure 4:
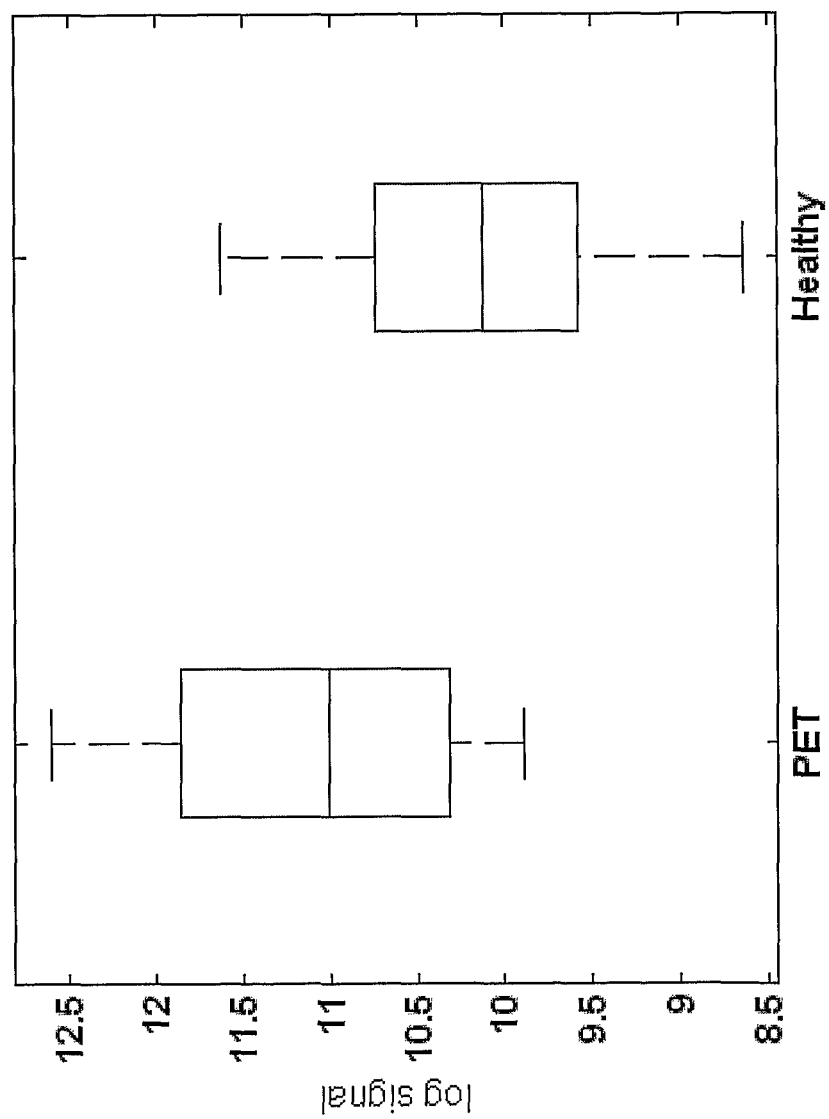
FIG. 4 shows differential expression of hsa-miR-210 (SEQ ID NO: 7) based on biochip array of placenta samples obtained from women with severe preeclampsia (PET) and healthy women underwent cesarean section prior to spontaneous onset of delivery (t-test p-value<0.015).
Figure 5:
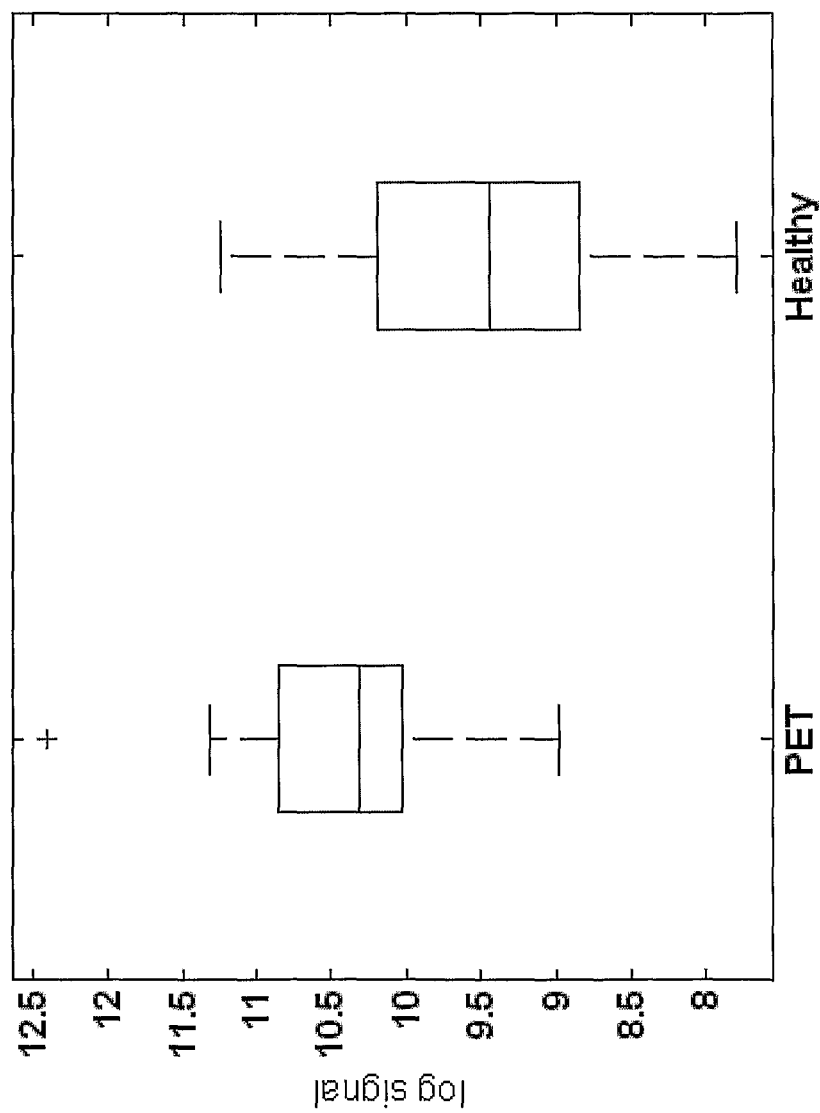
FIG. 5 shows differential expression of hsa-miR-193b* (SEQ ID NO: 8) based on biochip array of placenta samples obtained from women with severe preeclampsia (PET) and healthy women underwent cesarean section prior to spontaneous onset of delivery (t-test p-value<0.015).
Figure 6:
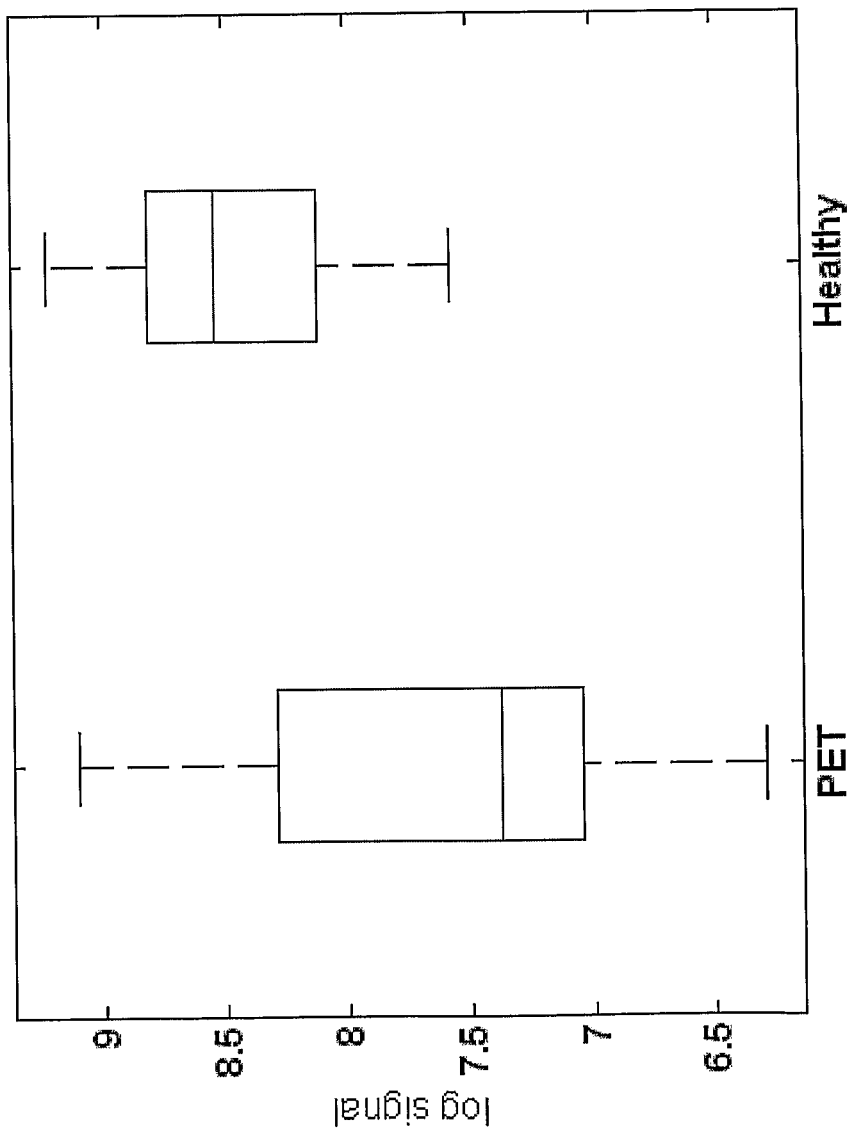
FIG. 6 shows differential expression of hsa-miR-652 (SEQ ID NO: 9) based on biochip array of placenta samples obtained from women with severe preeclampsia (PET) and control healthy women underwent cesarean section prior to spontaneous onset of delivery (t-test p-value<0.015).

The median fold changes in microRNA levels comparing third trimester pregnant women to non pregnant women are detailed in Table 1. Box plots show relative microRNA expression levels in the sera of 10 non pregnant women, 10 women in the first trimester and 10 women in the third trimester (FIG. 1A). Hsa-miR-526a (SEQ ID NO: 75) and hsa-miR-527 (SEQ ID NO: 53) are upregulated dramatically in the serum of third trimester pregnant women (more than 600 fold), and the expression levels of several other microRNAs are also significantly increased during pregnancy (Table 1 and FIG. 1A). The expression levels of the placental microRNAs rise with gestational age (FIG. 1A). Indeed, we found that the expression levels of three placental microRNAs (hsa-miR-526a, hsa-miR-527 and hsa-miR-520d-5p) could be used to accurately distinguish pregnant from non pregnant women (FIG. 1C) and even to identify different stages of pregnancy.

We have developed highly sensitive methods that enable the extraction and measurement of cell-free microRNAs in body fluids. Here, we establish that microRNAs are indeed present in serum and in other body fluids. We show that microRNA levels in serum are consistent across individuals and stable during routine processing of clinical samples. Importantly, we demonstrate that certain microRNAs in serum are expressed differentially under dissimilar physiological conditions, namely during pregnancy. Thus, circulating microRNAs represent promising candidates for robust, sensitive and easily accessible biomarkers.

TABLE 1 microRNA expression level comparison between non-pregnant and 3$^{rd}$ trimester women

| microRNA | miR SEQ ID NO: | Hairpin SEQ ID NO: | delta $C_T$ | fold change | p-value |
|---|---|---|---|---|---|
| hsa-miR-526a | 75 | 76 77 | 9.44 | 694 | 2.10E−07 |
| hsa-miR-527 | 53 | 54 | 9.28 | 622 | 1.20E−14 |
| hsa-miR-515-5p | 1 | 108 109 | 9 | 511 | 6.90E−08 |
| hsa-miR-521 | 21 | 26 | 7.36 | 164 | 8.10E−09 |
| hsa-miR-523 | 2 | 27 | 4.81 | 28 | 2.20E−06 |
| hsa-miR-524* | 3 | 28 | 4.81 | 27 | 2.80E−03 |
| hsa-miR-518a-3p | 106 | 55 56 | 3.61 | 12 | 1.80E−04 |
| hsa-miR-520d-5p | 69 | 70 | 3.1 | 8.6 | 3.30E−07 |
| hsa-miR-525-3p | 80 | 81 | 2.73 | 6.6 | 5.60E−04 |
| hsa-miR-526c | 91 | 92 | 2.47 | 5.5 | 1.10E−01 |
| hsa-miR-519e* | 82 | 83 | 2.38 | 5.2 | 1.30E−04 |
| hsa-miR-518d | 84 | 85 | 2.35 | 5.1 | 7.60E−03 |
| hsa-miR-524 | 110 | 28 | 2.27 | 4.8 | 3.80E−03 |
| hsa-miR-512-3p | 86 | 87 88 | 2.16 | 4.5 | 1.90E−03 |
| hsa-miR-141 | 78 | 79 | 2 | 4.0 | 3.90E−04 |
| hsa-miR-519d | 89 | 90 | 1.9 | 3.7 | 2.60E−02 |
| hsa-miR-517* | 93 | 94 | 1.82 | 3.5 | 5.80E−02 |
| hsa-miR-518e | 107 | 92 | 1.5 | 2.8 | 3.50E−02 |
| hsa-miR-145 | 95 | 96 | 0.98 | 2.0 | 3.20E−02 |
| hsa-miR-149 | 71 | 72 | 0.92 | 1.9 | 6.00E−01 |
| hsa-let-7d | 51 | 52 | 0.59 | 1.5 | 5.20E−01 |
| hsa-miR-16 | 97 | 98 99 | 0.39 | 1.3 | 6.90E−01 |
| hsa-miR-126 | 100 | 101 | 0.16 | 1.1 | 1.60E−01 |
| hsa-miR-451 | 4 | 29 | 0.13 | 0.91 | 8.40E−01 |
| hsa-miR-572 | 102 | 103 | 0.11 | 1.1 | 8.70E−01 |
| hsa-miR-202 | 104 | 105 | 0.1 | 1.1 | 4.80E−01 |

For each microRNA, "delta $C_T$" indicates the difference in median $C_T$ between the serum of pregnant women in the third trimester (n=10) and non-pregnant women (n=10). For each sample, the relative amount of the microRNAs was normalized by subtracting the average $C_T$ of the non-placenta-specific microRNAs. The fold change is the ratio of the median abundance in linear space, equal to the exponent (base 2) of the delta $C_T$. P-values are calculated by a two-sided unpaired t-test.

Example 3

Differential Expression of microRNAs in Placenta and Serum Samples Obtained from Women with Severe Preeclampsia (PET) and Healthy Women Overall 33 female patients were evaluated, among them 15 with severe PET and 18 served as control. Significant difference in microRNAs expression profile was found in placentas derived from patients with PET in comparison to the control group.

Figure 7:
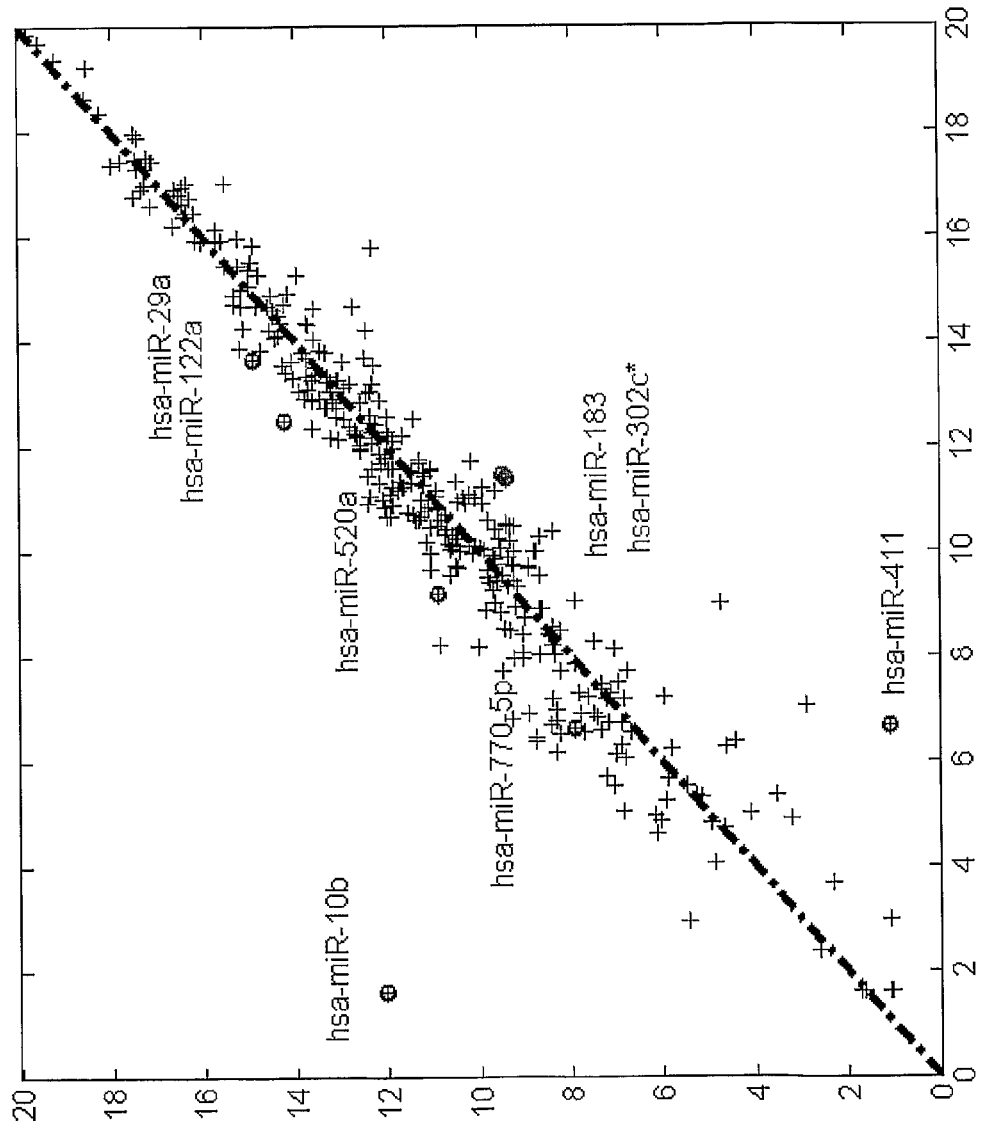
FIG. 7 shows the average microRNA expression levels (50-Ct) based on qRT-PCR analysis of serum samples obtained from women with severe preeclampsia (PET) (y-axis) and from healthy women (x-axis) underwent cesarean section prior to spontaneous onset of delivery. Differentially expressed microRNAs are marked by circles (t-test p-value<0.05).
Figure 8:
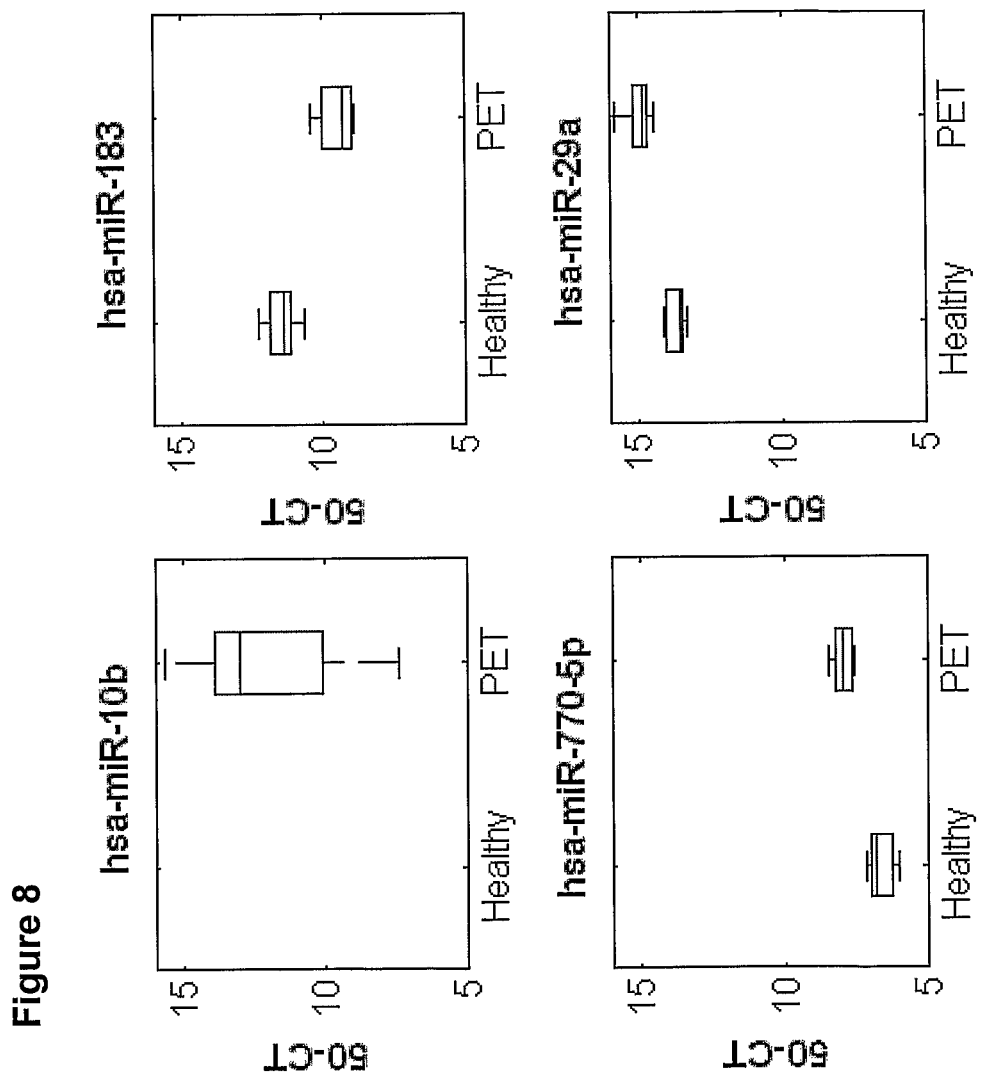
FIG. 8 shows differential expression of hsa-miR-10b (SEQ ID NO:10), hsa-miR-183 (SEQ ID NO: 11), hsa-miR-770-5P (SEQ ID NO:12) and hsa-miR-29a (SEQ ID NO: 13) in serum samples obtained from women with severe preeclampsia (PET) and control healthy women underwent cesarean section prior to spontaneous onset of delivery (West p-value<0.015).
Figure 9:
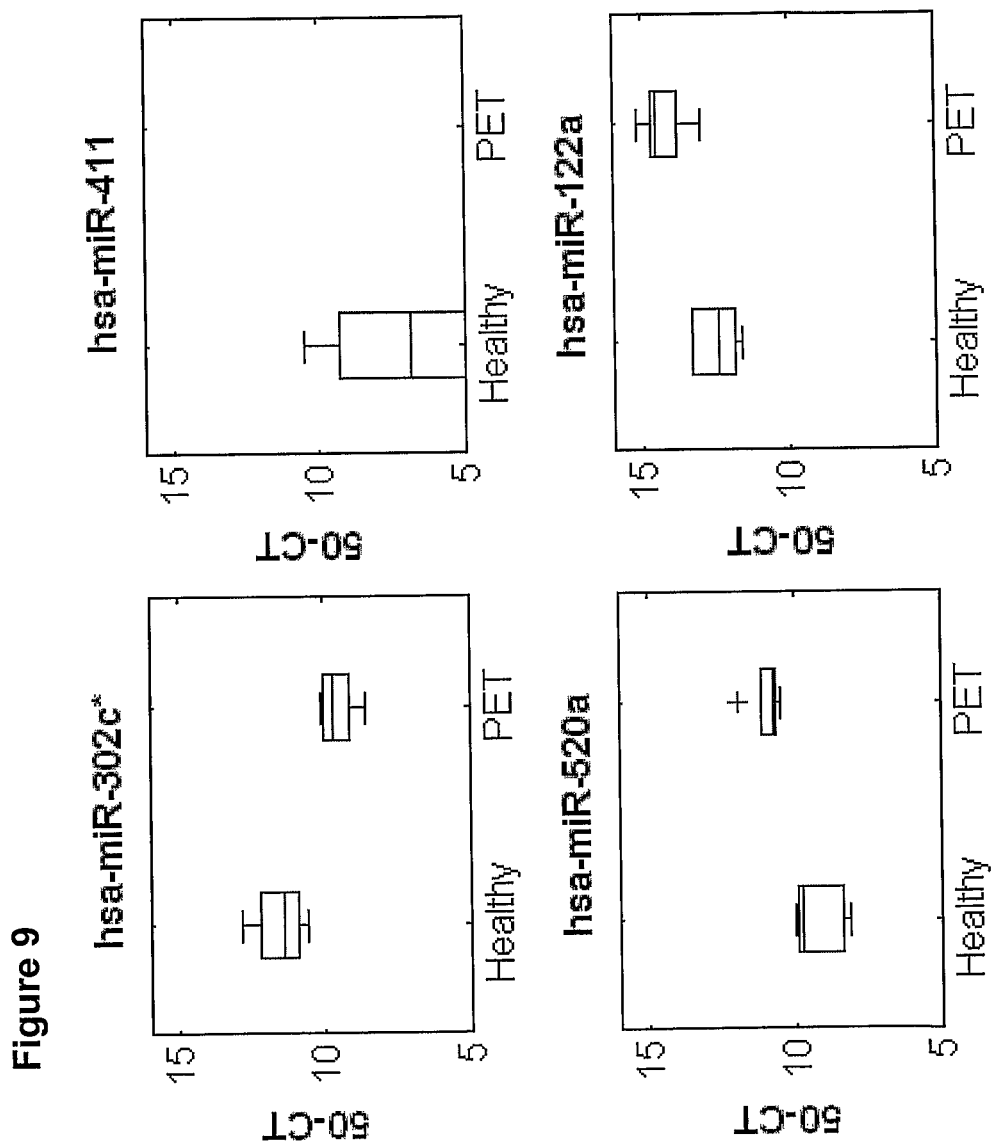
FIG. 9 shows differential expression of hsa-miR-302c* (SEQ ID NO: 14), hsa-miR-411 (SEQ ID NO: 15), hsa-miR-520a (SEQ ID NO: 16) and hsa-miR-122a (SEQ ID NO: 17) in serum samples obtained from women with severe preeclampsia (PET) and control healthy women underwent cesarean section prior to spontaneous onset of delivery (t-test p-value<0.015).

As shown in FIGS. 3-6, hsa-miR 31 (SEQ ID NO: 5), ambi-miR-7510 (SEQ ID NO:6), hsa-mir-210 (SEQ ID NO:7), hsa-mir-193b* (SEQ ID NO:8) were significantly downregulated in placentas derived from patients with PET and hsa-mir-652 (SEQ ID NO:9) was found to be significantly upregulated.

qRT-PCR analysis of 400 microRNAs was preformed on serum samples obtained from women with severe preeclampsia (PET) or from control healthy women underwent cesarean section prior to spontaneous onset of delivery. The average microRNA expression levels (50-Ct) of serum samples obtained from women with severe preeclampsia (PET) (y-axis) and from healthy women (x-axis) is presented in FIGS. 7-9. Differentially expressed microRNAs (hsa-miR-10b (SEQ ID NO:10), hsa-miR-183 (SEQ ID NO:11), hsa-miR-770-5P (SEQ ID NO:12), hsa-miR-29a (SEQ ID NO:13), hsa-miR-302c* (SEQ ID NO:14), hsa-miR-411 (SEQ ID NO:15), hsa-miR-520a (SEQ ID NO:16) and hsa-miR-122a (SEQ ID NO:17)) are marked by circles (t-test p-value<0.05).

These findings suggest that specific microRNAs may play an essential role in the pathogenesis and diagnosis of PET.

Example 4

Differential Expression of microRNAs in Specimen of Uterine Myometrium and Placenta Obtained from Women with Spontaneous Preterm Onset of Delivery (sPTL) and from Control Group Overall 10 female patients were evaluated, among them 5 with spontaneous preterm onset of delivery and 5 women delivering at term served as control. Significant difference in microRNAs expression profiles was found in placentas and uterine myometrium derived from patients with sPTL in comparison to the control group.

Figure 10:
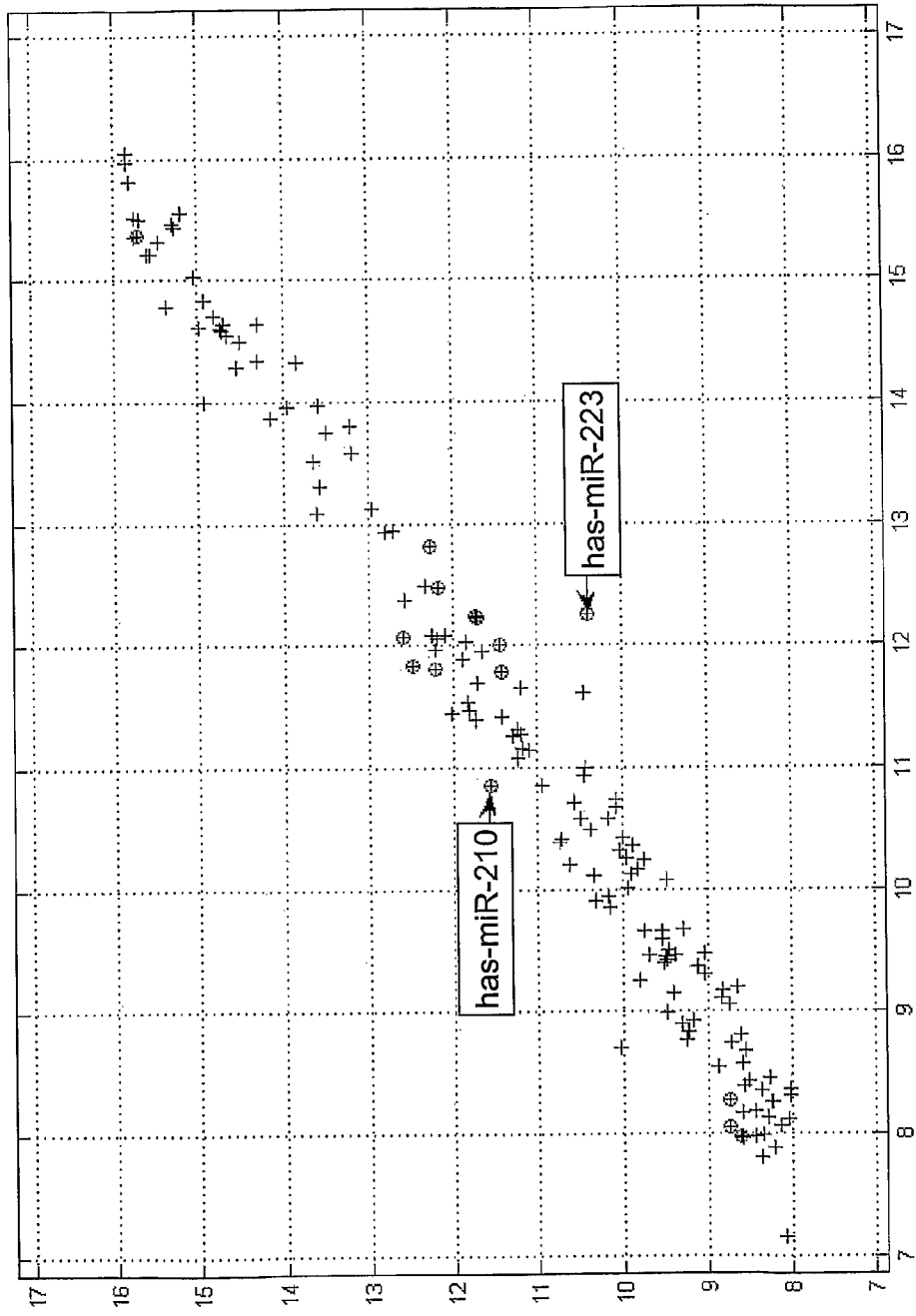
FIG. 10 shows the average microRNA expression levels based on biochip array of specimen of uterine myometrium obtained from women with spontaneous preterm onset of delivery (sPTL) (x-axis) and from control women delivered by cesarean section at term (y-axis). Differentially expressed microRNAs (hsa-miR-210 (SEQ ID NO: 18) and hsa-miR-223 (SEQ ID NO: 19)) are marked by circles (t-test p-value<0.05).

As shown in FIG. 10, hsa-miR 210 (SEQ ID NO: 18) and hsa-miR-223 (SEQ ID NO: 19) are differentially expressed in specimen of uterine myometrium obtained from women with sPTL in comparison to control group.

Figure 11:
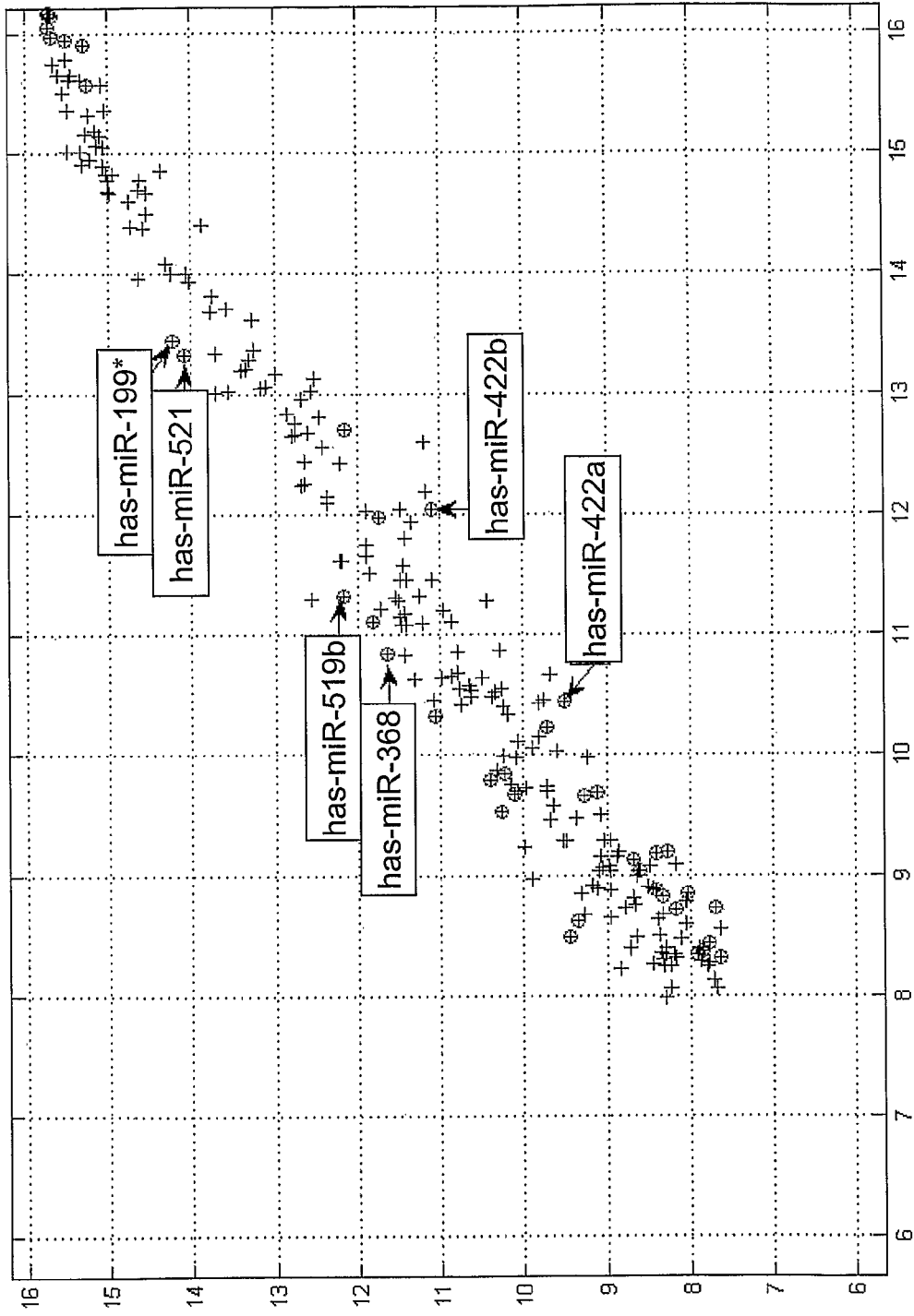
FIG. 11 shows the average microRNA expression levels based on biochip array of specimen of placenta obtained from women with spontaneous preterm onset of delivery (sPTL) (x-axis) and from control women delivered by cesarean section at term (y-axis). Differentially expressed microRNAs (hsa-miR-199a* (SEQ ID NO: 20), hsa-miR-521 (SEQ ID NO: 21), hsa-miR-519b (SEQ ID NO: 22), hsa-miR-368 (SEQ ID NO: 23), hsa-miR-422a (SEQ ID NO: 24) and hsa-miR-422b (SEQ ID NO: 25)) are marked by circles (t-test p-value<0.05).

As shown in FIG. 11, hsa-miR-199* (SEQ ID NO: 20), hsa-miR-521 (SEQ ID NO: 21), hsa-miR-519b (SEQ ID NO: 22), hsa-miR-368 (SEQ ID NO: 23), hsa-miR-422a (SEQ ID NO: 24) and hsa-miR-422b (SEQ ID NO: 25) are differentially expressed in specimen of placentas obtained from women with sPTL in comparison to control group.

These findings suggest that specific microRNAs may play an important role in the regulation and the detection of sPTL.

The invention claimed is:

1. A method for determining whether a pregnant female subject is at risk of developing preeclampsia, and a treatment strategy for said female subject based on said determination comprising: obtaining a biological test sample from said female subject and a control biological sample from a pregnant woman of same gestational age with no clinical or laboratory evidence of hypertensive disorder of pregnancy; extracting microRNA molecules from the test biological sample and the control biological sample; determining the expression of the nucleic acid sequence SEQ ID NO: 17 in the test biological sample and the control biological sample; determining whether said pregnant female subject is at risk of developing preeclampsia based on increased expression of SEQ ID NO: 17 in the test biological sample relative to the control biological sample; and determining a treatment strategy for said pregnant female based on the increased expression of SEQ ID NO: 17 in the test biological sample relative to the control biological sample.

2. The method of claim 1, wherein said biological sample is selected from the group consisting of bodily fluid and a tissue sample.

3. The method of claim 2, wherein said tissue is a fresh, frozen, fixed, wax-embedded or formalin fixed paraffin-embedded (FFPE) tissue.

4. The method of claim 3, wherein said tissue sample is placenta sample or uterine myometrium sample.

5. The method of claim 2, wherein said bodily fluid sample is serum sample.

6. The method of claim 1, wherein the expression is determined by a method selected from the group consisting of nucleic acid hybridization and nucleic acid amplification.

7. The method of claim 6, wherein the nucleic acid hybridization is performed using a solid-phase nucleic acid biochip array or in situ hybridization.

8. The method of claim 6, wherein the nucleic acid amplification method is real-time PCR.

* * * * *